United States Patent
Fearnot et al.

(10) Patent No.: US 12,383,223 B2
(45) Date of Patent: Aug. 12, 2025

(54) PERCUTANEOUS, ULTRASOUND-GUIDED INTRODUCTION OF MEDICAL DEVICES

(71) Applicant: Muffin Incorporated, West Lafayette, IN (US)

(72) Inventors: Neal E. Fearnot, West Lafayette, IN (US); Peter S. McKinnis, Carrboro, NC (US); Kasper Klausen, Lille Skensved (DK)

(73) Assignee: Muffin Incorporated, West Lafayette, IN (US)

( * ) Notice: Subject to any disclaimer, the term of this patent is extended or adjusted under 35 U.S.C. 154(b) by 869 days.

(21) Appl. No.: 16/174,395

(22) Filed: Oct. 30, 2018

(65) Prior Publication Data

US 2019/0261943 A1     Aug. 29, 2019

Related U.S. Application Data

(63) Continuation of application No. 13/731,313, filed on Dec. 31, 2012, now Pat. No. 10,111,645, which is a
(Continued)

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/463* (2013.01); *A61B 8/5238* (2013.01);
(Continued)

(58) Field of Classification Search
CPC .... A61B 2034/2063; A61B 2034/2065; A61B 2090/378; A61B 2090/3782;
(Continued)

(56) References Cited

U.S. PATENT DOCUMENTS 5,114,401 A     5/1992 Stuart et al.
5,257,629 A *   11/1993 Kitney ................. A61B 8/4494
                                                    600/463
(Continued)

FOREIGN PATENT DOCUMENTS

CN     101450019       6/2009
CN     101754727 A     6/2010
(Continued)

OTHER PUBLICATIONS

International Application No. PCT/US2011/042670 International Search Report and Written Opinion, mailed Jul. 27, 2012, 18 pgs.

*Primary Examiner* — Keith M Raymond
*Assistant Examiner* — Milton Truong
(74) *Attorney, Agent, or Firm* — Woodard Emhardt Henry Reeves & Wagner LLP

(57) ABSTRACT

Described are methods and systems and system components useful for percutaneously delivering or retrieving vascular implant devices, such as filters, utilizing intravenous ultrasound (IVUS) imaging alone or in combination with external (e.g. transabdominal) ultrasound or other imaging technology. Implants deliverable by such systems, such as vena cava or other vascular filters, can have two or more echogenic markers spaced at such a distance that they are separately discernible by IVUS and/or external ultrasound imaging.

19 Claims, 20 Drawing Sheets

Related U.S. Application Data continuation of application No. PCT/US2011/042670, filed on Jun. 30, 2011.

(60) Provisional application No. 61/406,418, filed on Oct. 25, 2010, provisional application No. 61/360,459, filed on Jun. 30, 2010.

(51) Int. Cl.
  *A61B 8/12* (2006.01)
  *A61B 34/20* (2016.01)
  *A61B 90/00* (2016.01)
  *A61F 2/01* (2006.01)

(52) U.S. Cl.
  CPC ...... *A61B 34/20* (2016.02); *A61B 2034/2063* (2016.02); *A61B 2034/2065* (2016.02); *A61B 2090/3784* (2016.02); *A61B 2090/3788* (2016.02); *A61B 2090/3925* (2016.02); *A61B 2090/3966* (2016.02); *A61F 2/011* (2020.05); *A61F 2002/016* (2013.01); *A61F 2230/005* (2013.01); *A61F 2230/0067* (2013.01); *A61F 2230/008* (2013.01)

(58) Field of Classification Search
  CPC .... A61B 2090/3784; A61B 2090/3786; A61B 2090/3788; A61B 2090/3925; A61B 2090/3966; A61B 34/20; A61B 8/0841; A61B 8/12; A61B 8/463; A61B 8/5238; A61B 2034/107; A61B 2090/365; A61F 2/011; A61F 2002/016; A61F 2230/005; A61F 2230/0067; A61F 2230/008
  See application file for complete search history.

(56) References Cited

U.S. PATENT DOCUMENTS

| | | | |
|---|---|---|---|
| 6,080,178 A | 6/2000 | Meglin | |
| 6,275,724 B1 | 8/2001 | Dickinson et al. | |
| 6,440,077 B1 | 8/2002 | Jung et al. | |
| 2002/0049375 A1* | 4/2002 | Strommer | A61B 8/0841 600/407 |
| 2002/0095141 A1 | 7/2002 | Belef et al. | |
| 2002/0120323 A1 | 8/2002 | Thompson et al. | |
| 2002/0143362 A1 | 10/2002 | Macoviak et al. | |
| 2002/0161394 A1 | 10/2002 | Macoviak et al. | |
| 2004/0143290 A1 | 7/2004 | Brightbill | |
| 2004/0215071 A1* | 10/2004 | Frank | A61B 6/463 600/407 |
| 2005/0107688 A1 | 5/2005 | Strommer | |
| 2006/0069405 A1 | 3/2006 | Schaeffer et al. | |
| 2006/0129180 A1 | 6/2006 | Tsugita et al. | |
| 2006/0178626 A1 | 8/2006 | Axelsson et al. | |
| 2006/0241465 A1* | 10/2006 | Huennekens | A61B 6/487 600/458 |
| 2006/0253029 A1* | 11/2006 | Altmann | A61B 8/12 600/466 |
| 2006/0253032 A1 | 11/2006 | Altmann et al. | |
| 2006/0259137 A1 | 11/2006 | Artof et al. | |
| 2006/0287595 A1* | 12/2006 | Maschke | A61B 8/12 604/95.01 |
| 2007/0208252 A1* | 9/2007 | Makower | A61B 6/032 606/198 |
| 2007/0265564 A1 | 11/2007 | Daly et al. | |
| 2008/0009747 A1 | 1/2008 | Saadat et al. | |
| 2008/0021552 A1 | 1/2008 | Gabbay | |
| 2008/0033397 A1 | 2/2008 | Serino et al. | |
| 2008/0132933 A1 | 6/2008 | Gerber | |
| 2008/0177180 A1* | 7/2008 | Azhari | A61B 8/406 600/439 |
| 2008/0208133 A1 | 8/2008 | Lieberman et al. | |
| 2009/0018638 A1 | 1/2009 | Shirley et al. | |
| 2009/0054922 A1 | 2/2009 | Broker | |
| 2009/0088648 A1* | 4/2009 | Jaffe | A61B 5/0084 600/466 |
| 2009/0143849 A1 | 6/2009 | Ozawa et al. | |
| 2009/0149938 A1 | 6/2009 | Grewe et al. | |
| 2009/0264826 A1 | 10/2009 | Thompson | |
| 2010/0048996 A1* | 2/2010 | Makiyama | A61B 1/00133 600/114 |
| 2010/0234724 A1* | 9/2010 | Jacobsen | A61B 34/20 600/424 |
| 2010/0268265 A1 | 10/2010 | Krolik et al. | |
| 2010/0298695 A1* | 11/2010 | Wenger | A61B 34/20 600/424 |
| 2016/0066881 A1* | 3/2016 | Li | A61B 8/12 600/443 |
| 2016/0331469 A1* | 11/2016 | Hall | A61B 8/0841 |

FOREIGN PATENT DOCUMENTS

| | | |
|---|---|---|
| EP | 1 416 443 A1 | 5/2004 |
| JP | 2008-513147 A | 5/2008 |
| WO | WO 1996/25882 | 8/1996 |
| WO | WO 1999/016382 | 4/1999 |
| WO | WO 2000/042926 | 7/2000 |
| WO | WO 2003/073961 A1 | 9/2003 |
| WO | WO 2003/090834 A3 | 11/2003 |
| WO | WO 2004/084737 A1 | 10/2004 |
| WO | WO 2005/102211 A1 | 11/2005 |
| WO | WO 2006/034233 A1 | 3/2006 |
| WO | WO 2006043276 A3 | 4/2006 |
| WO | WO 2007/143602 | 12/2007 |
| WO | WO 2008/147602 | 12/2008 |
| WO | WO 2009/044316 A1 | 4/2009 |
| WO | WO 2009/076482 A1 | 6/2009 |

* cited by examiner

PERCUTANEOUS, ULTRASOUND-GUIDED INTRODUCTION OF MEDICAL DEVICES

REFERENCE TO RELATED APPLICATION

This application is a continuation U.S. patent application Ser. No. 13/731,313, filed Dec. 31, 2012 which is a continuation of International Application No. PCT/US2011/042670, filed Jun. 30, 2011, which claims the benefit of U.S. Provisional Patent Application Ser. No. 61/360,459 filed Jun. 30, 2010 and of U.S. Provisional Patent Application No. 61/406,418 filed Oct. 25, 2010, each entitled Percutaneous, Ultrasound-Guided Introduction of Medical Devices, and each of which is hereby incorporated herein by reference in its entirety.

BACKGROUND

The present invention pertains generally to medical devices and systems for their introduction. In certain aspects, the invention relates to systems and methods for percutaneously introducing vascular devices such as vascular filters under ultrasound guidance, and to delivery components and implant features that are useful therein.

Vascular devices are commonly percutaneously introduced under fluoroscopic guidance. For example, vena cava filters are most often placed under fluoroscopic guidance with the injection of contrast agent to provide a cavogram characterizing the site of intended implantation. Such fluoroscopic procedures must be performed in a specially equipped room such as an X-ray suite. This not only necessitates transport of an often critically ill patient to the suite but also adds significant expense to the procedure.

Ultrasound imaging technology, including intravenous ultrasound (IVUS) imaging, has been used to some extent in the diagnosis and in the treatment of patients. However, the images generated with IVUS and other ultrasound technology are often more difficult to interpret for purposes of implant guidance, particularly for physicians or other health care providers who are more accustomed to fluoroscopic images.

Needs exists for improved and/or alternative methods, systems and device features whereby the introduction of vascular devices such as vena cava filters can be guided under ultrasound imaging techniques. In certain of its aspects, the present invention is addressed to these needs.

SUMMARY

In some embodiments, the present invention relates to methods and systems for percutaneously delivering or retrieving vascular implant devices, such as filters, utilizing intravenous ultrasound (IVUS) imaging alone or in combination with external (e.g. transabdominal) ultrasound imaging technology. Delivery systems of the invention can include distally-positioned echogenic markers and proximally-positioned visible indicia which together provide enhanced guidance during implant introduction. Implants deliverable by such systems, such as vena cava or other vascular filters, can have two or more echogenic markers spaced at such a distance that they are separately discernible by IVUS and/or external ultrasound imaging. Additional embodiments include IVUS-enabled catheters, IVUS-enabled sheaths, and IVUS-enabled vascular snares, useful for example in the placement or retrieval of vena cava filters, and IVUS-facilitated confirmation of device placement following deployment and systems therefor.

Ultrasound-guiding systems and methods described herein can utilize a combination of IVUS and external (e.g. transabdonimal) ultrasound images, real-time-generated images and stored images (e.g. three-dimensional maps) generated using IVUS imaging, and/or a combination of IVUS images and displayed graphical markers generated by non-imaging techniques. Still further aspects of the invention, and features and advantages thereof, will be apparent to those of ordinary skill in the art from the description herein.

DETAILED DESCRIPTION

Figure 1:
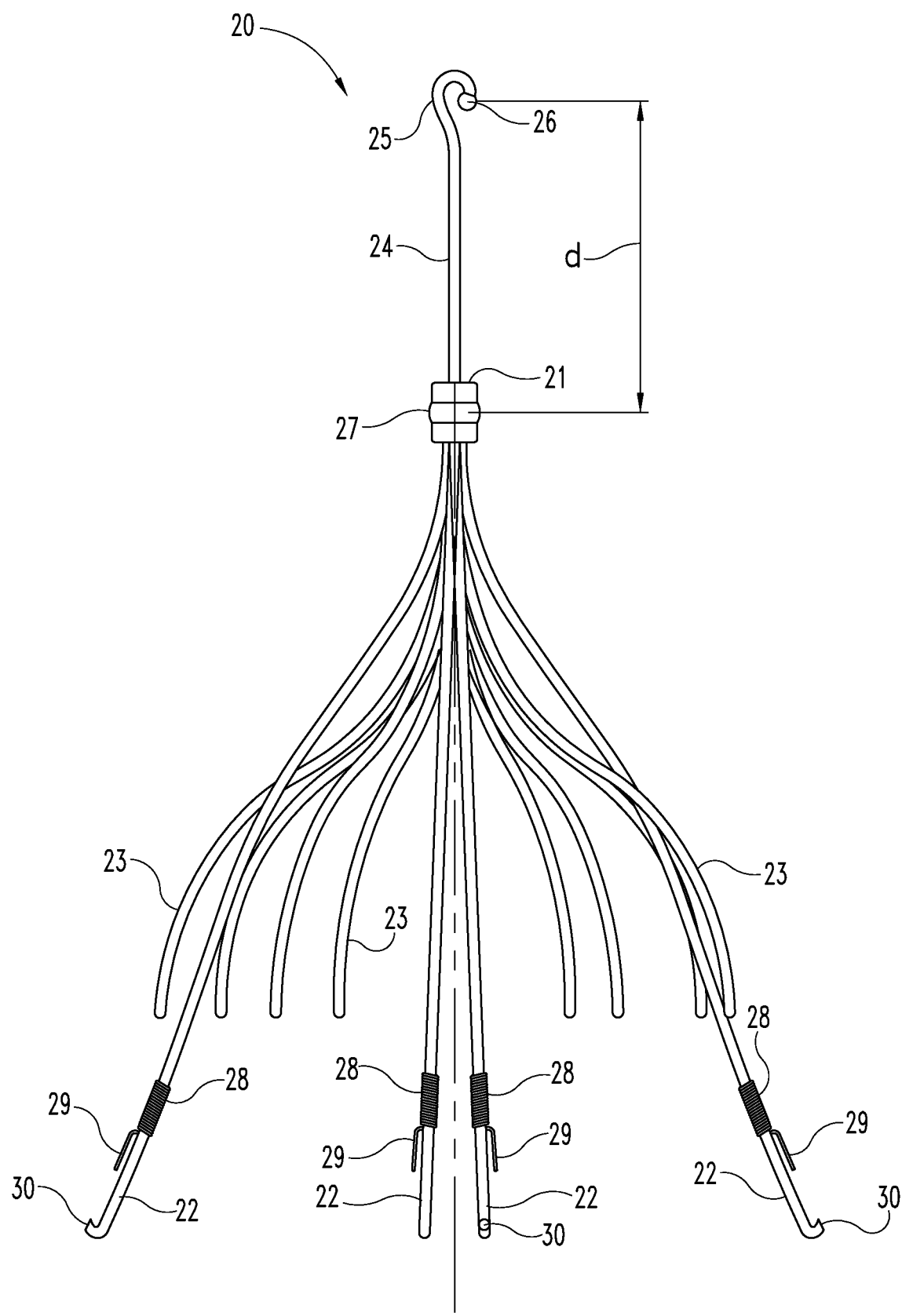
FIG. 1 is a perspective view of one embodiment of a filter device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As disclosed above, certain aspects of the invention relate to methods and systems that include features which enhance functionality and/or safety during delivery of the vascular devices using ultrasound imaging techniques. Additionally, aspects of the invention relate to vascular devices, and in particular embodiments vascular filters, including two or more echogenic markers located thereon, as well as percutaneous delivery or retrieval devices that include unique echogenic features and/or IVUS imaging capability.

With reference now to FIG. 1, shown is a vascular filter 20 in an expanded state. Vascular filter 20 as depicted is suitable for use as a vena cava filter in humans. Filter 20 includes a hub 21 having a plurality of primary struts 22 and plurality of secondary struts 23 emanating therefrom. In particular, in the depicted embodiment, filter 20 includes four primary struts 21 and eight secondary struts 23 extending from hub 21. Hub 21 crimps together ends of struts 22 and 23 in a compact bundle extending generally along a central or longitudinal axis of filter 20. The struts 22 and 23 can be formed of a superelastic metal alloy, such as a superelastic nickel-titanium (Ni—Ti) alloy (e.g. Nitinol), stainless steel, or any other suitable material that will result in a self-expanding filter. The struts of filter 20 can provide a filter structure configured to trap embolic matter in the vascular vessel. Other filters of the invention can include alternate strut configurations or other member(s) positionable within the vessel to trap embolic matter.

Filter 20 also includes a retrieval/delivery element including a generally straight elongate neck 24 connected to a reversely-turned hook 25, with the hook terminating in ball component 26. This retrieval/delivery feature can be used in retrieving and/or initially placing the filter 20. Although neck 24 as illustrated is generally straight, it will be understood that other neck configurations, including curved configurations, can be used. Hub 21 includes a shoulder 27 or other feature, preferably extending around its entire circumference, that serves as an echogenic marker and thus generates an ultrasound image discernable from surrounding media or device components. In addition, ball component 26 effectively serves as such an echogenic marker.

In the illustrated device, shoulder 27 and ball 26, or other echogenic features in their place, are longitudinally spaced a distance "d" from one another sufficient to enable separate and discrete visualization of ball/marker 26 and shoulder/marker 27 by IVUS imaging, external ultrasound imaging, or both. In particular embodiments, when using IVUS imaging, distance "d" is sufficiently great that the IVUS probe for generating the IVUS image can be positioned within longitudinal distance "d" without picking up either ball/marker 26 or shoulder/marker 27 in the image. In this manner, the IVUS probe and other device components adjacent thereto (e.g. the tip of a snare catheter) can be reliably and recognizably positioned within longitudinal distance "d" by advancing or withdrawing the IVUS probe to separately view ball/marker 26 and shoulder/marker 27, and then positioning the IVUS probe therebetween to a point where neither marker is visible in the IVUS image. The attending physician or other user can thereby develop confidence that the IVUS probe and device components nearby are properly positioned for action within the span of longitudinal distance "d". Illustratively, as discussed in greater detail below, a retrieval snare having an IVUS probe at or near its distal tip can be reliably positioned within longitudinal distance "d" for closure of a snare loop to capture the retrieval element of filter 20. In addition or alternatively, distance "d" can be sufficiently large that marker 26 and marker 27 generate separate and discrete images using external (e.g. transabdominal) imaging techniques. External imaging can then be used to view the positioning of third echogenic marker, for example on another device such as the end of a snare, between marker 26 and 27, for action within the span of distance "d". In certain embodiments, distance "d" is greater than 3 mm, for example in the range of 4 mm to 10 mm.

Filter 20 may also have echogenic markers positioned on one or a plurality of its primary and/or secondary struts. These echogenic markers can for example be echogenic elements mounted around the struts, including for example sonically-reflective metal coils discernable by IVUS or external ultrasound (US) imaging, or cannular segments with dimpled, grooved or otherwise textured surfaces, or any other suitable echogenic structure. In the illustrated device, echogenic coils 28 are mounted around the primary struts 22. Further, echogenic markers 28 can include projecting filaments such as whiskers or barbs 29, which can serve to enhance interaction of the struts with the vessel walls, for example providing improved anchorage and/or resistance to strut migration through the vessel walls.

Figure 1A:
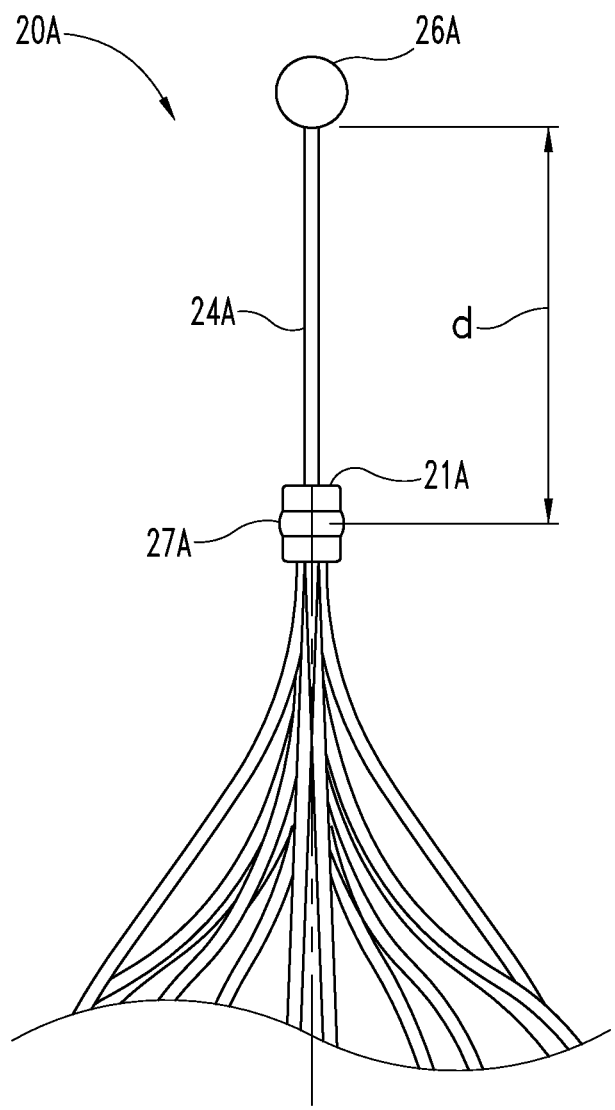
FIG. 1A is a partial cut-away view of another embodiment of a filter device.
Figure 1B:
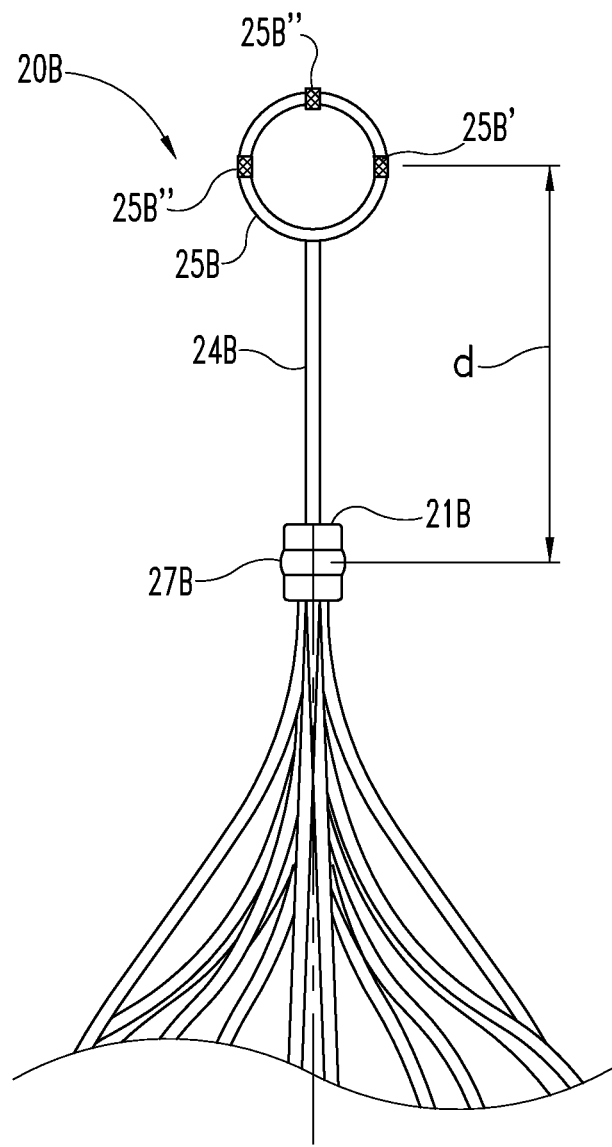
FIG. 1B is a partial cut-away view of another embodiment of a filter device.

Referring now to FIGS. 1A and 1B, shown are a partial cutaway views of additional embodiment of filters 20A and 20B of the invention, respectively. Except where described otherwise, filters 20A and 20B can have features that are the same as those of filter 20. In filter 20A, a delivery/retrieval element is provided that includes a shoulder 27A on the hub as in filter 20, and a generally straight neck portion 24A connected to a terminating, larger-diameter ball component 25A. Ball component 25A is of sufficient dimension to serve as a graspable feature utilizing a vascular snare. Ball component 25A also serves as an echogenic marker for the filter 20A. In filter 20B (FIG. 1B), a delivery/retrieval element is provided that includes a shoulder 27B on the hub as in filter 20, and a generally straight neck portion 24B connected to a terminating closed hoop 25B. Hoop 25B defines an internal opening and is of sufficient dimension to serve as a graspable feature, for example utilizing a retrieval hook device. Hoop component 25B also includes at least one echogenic marker thereon and in certain embodiments a plurality of echogenic markers (25B', 25B", 25B''') which may for example be any echogenic structure, component or material described herein, attached to or integrally occurring within or upon the material of hoop 25B.

While FIGS. 1, 1A and 1B illustrate specific retrieval elements for incorporation within the structure of the vascular filter, it will be understood that other retrieval structures or materials can also be used within aspects of the invention. For example, any attachment structure that can be engaged by mechanical elements and/or using field forces (e.g. magnetic), or by other means, can be used. In certain embodiments, as in the illustrated filters, the retrieval element of the filter can be configured to reside generally centrally in the vessel lumen when the filter is deployed.

Figure 2:
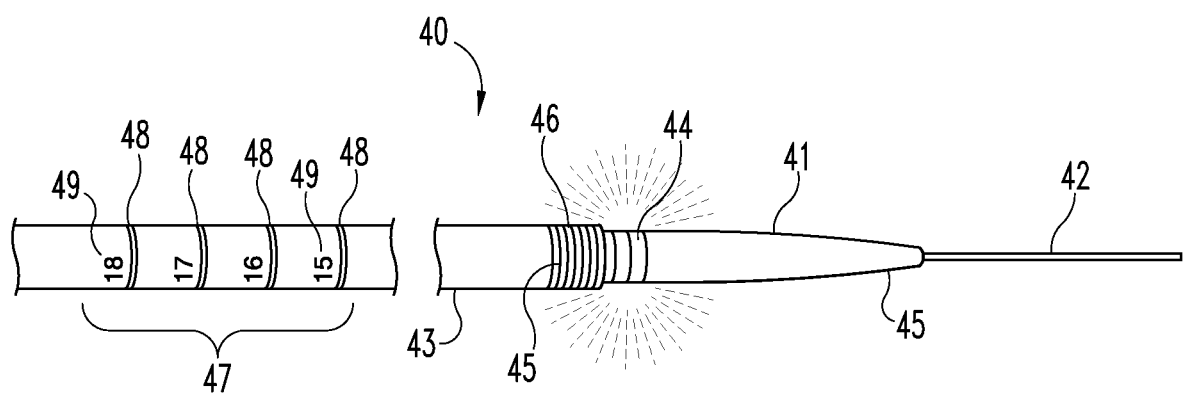
FIG. 2 is a partial cut-away perspective view of one embodiment of an IVUS-enabled device delivery system.

With reference to FIG. 2, shown is a partial cutaway view of a system useful for implanting a vascular device such as a filter. System 40 includes a dilator 41 for percutaneous introduction, a guide device 42 such as a wire guide, and an outer delivery sheath 43. Dilator 41 includes an IVUS probe 44 including one or more ultrasound transducers, such as piezoelectric crystal elements, for producing and/or receiving ultrasonic sound waves. IVUS probe 44 is preferably a transducer array with a plurality of ultrasound transducers, but can also be provided by a single rotating transducer as known. IVUS probe 44 and other IVUS elements disclosed herein can, for example, be configured to provide data for two-dimensional and/or three-dimensional IVUS images. IVUS probe 44 is connected electronically, such as by a wire and connector (not shown) positioned within or along dilator 41, to an IVUS imaging system that may include a display device and a computer processor for processing data gathered by IVUS probe 44 and displaying images correlated thereto. Sheath 43 of system 40 includes a distal tip region having an echogenic marker 45 and a fluoroscopic marker 46. Echogenic marker 45 and fluoroscopic marker 46 can be provided by the same physical structure or by differing physical structures.

In one embodiment, the markers 45/46 are both provided by a radiopaque material, such as platinum, titanium, tungsten or another a metal (including alloys), positioned outside and/or within the material making up the body of the sheath 43. Illustratively, a platinum structure, such as a platinum hoop or ring, can be attached around the outside of sheath 43 to provide a fluoroscopically-discernible marker. Such a radiopaque structure can also contain structural features rendering it effective as an echogenic marker. These features may for example include dimples, grooves, or other textured surface features rendering the marker material visually discernible by ultrasound imaging. The fluoroscopic and/or echogenic markers can also be provided by other structures or materials or combinations thereof. Illustratively, in one embodiment, the markers 45 and 46 can be located closely adjacent one another, with the fluoroscopic marker 46 provided by a radiopaque material such as a metal, and the echogenic marker 45 provided by a separate element with any of the patterned features as discussed hereinabove for echogenic markers, or containing internal materials or features that have an acoustic impedance that significantly differs from the surrounding media so as to be discernible by ultrasonic imaging. The incorporated features or materials can include for example gas-filled spaces embedded within polymeric materials (e.g. bubbles), or acoustic impedance-mismatched, sonically-reflective materials such as glass, ceramic, metal or other particles (e.g. beads) incorporated within or coated upon a polymeric material. For additional information about echogenic markers that can be used herein, reference can be made for example to U.S. Pat. No. 5,201,314.

The markers 45/46 can be associated with sheath 43 in any suitable fashion including positioning on the outside, inside, within the body or wall of the sheath 43, or combinations thereof. Sheath 43 also includes a more proximally located marking feature 47 that is visible to the eye of the user when positioned externally of the patient. Visible marking feature 47 in the illustrated embodiment demarks the distance from locations within feature 47 to the distal tip of the sheath 43. For these purposes, the marking feature 47 can include a plurality of visible marking features 48 spaced longitudinally from one another along the length of sheath 43, such as lines, scores, or other markings partially or completely circumscribing the circumference of the sheath 43. In the illustrated embodiment, the marking feature 47 also includes numeric markings 49 associated with markings 48 which numerically indicate the distance of the respective associated markings 48 from the tip of the sheath 43. In one example, the marking feature 47 includes markings 48 offset longitudinally from one another by a regular distance such as 1 mm or 1 cm, and associated numerical markings 49 providing an indication of how many millimeters or centimeters, respectively, each marking 48 is spaced from the distal tip of the sheath 43. The marking feature 47 is positioned along the length of the sheath 43 such that at least some of or the entire marking feature 47 will occur externally of the patient during use of the sheath 43 to deliver the filter or other vascular device. For these purposes, the marking feature 47 can for example be positioned so as to include markings at skin level at a percutaneous insertion site through which system 40 is introduced. In this regard, it will be understood that other reference points external of the patient against which the marking feature 47 can be reliably tracked during a procedure to determine the distance to the distal tip of the sheath may also be used. Fixed external reference points are particularly useful for these purposes.

In one mode of use, the IVUS-enabled dilator 41 can be advanced within a vascular vessel of the patient along guide 42, and the IVUS probe 44 can be operated to generate signals translated to images of features of the vessel. IVUS probe 44 can then be positioned to and image a target position to which it is desired to move the distal tip of the sheath 43. Thereupon, the sheath 43 can be advanced coaxially along the dilator 41 until the distal tip of the sheath 43 detectably abuts or overlies IVUS probe 44 or regions proximate thereto. This detection can, for example, be by way of a tactile resistance to advancement of the sheath 43 over the IVUS probe 44 or some region or feature of sheath 43 proximate thereto, or by a change in an ultrasound image generated based signals from IVUS probe 44 due to the distal tip of the sheath 43 overlying some or all of IVUS probe 44 (for example, a change in the brightness of the image). This change in the image, in certain embodiments, can be enhanced by the presence of the echogenic marker 45 at the distal end region of sheath 43. At this point, the user knows that the distal tip of the sheath 43 is in essentially the same target position as the IVUS probe 44. Thereafter, the dilator 41 and guide 42 can be withdrawn from sheath 43, and a delivery catheter or other delivery instrument for delivering the vascular device can be advanced through sheath 43, while continuing to hold stable the position of the sheath 43 with its distal tip at the target position. In certain embodiments, the distal tip of the vascular implant to be deployed can then be aligned with the distal tip of the sheath 43 while maintaining the stable position of the sheath 43, and sheath 43 can be withdrawn proximally a distance while holding stable the position of the delivery instrument to reliably deploy the vascular device at the target site.

The alignment of the distal end of the vascular implant with the distal end of the sheath 43 can be accomplished in any suitable manner, including by tracking the position of the distal tip of the vascular implant ultrasonically (e.g. transabdominally with the assistance of a tip-located echogenic markers, such as marker 26 on filter 20 and marker 45 on sheath 43) and/or through other means. In certain embodiments, the vascular device is carried by a delivery catheter or other instrument having a first visible marker that remains external of the patient and which aligns with an external reference point, such as the proximal end of the sheath 43 or a connected accessory (e.g. a Touhy-Borst adaptor), when the distal end of the vascular implant is at the distal tip of the sheath 43. The delivery instrument may also include a second visible marker, proximal to the first visible marker, to which the sheath can be withdrawn, to signal a stage of deployment, e.g. when the vascular implant has been completely deployed out of the sheath. Other measures for accomplishing similar signaling alignments may also be used.

Figure 3:
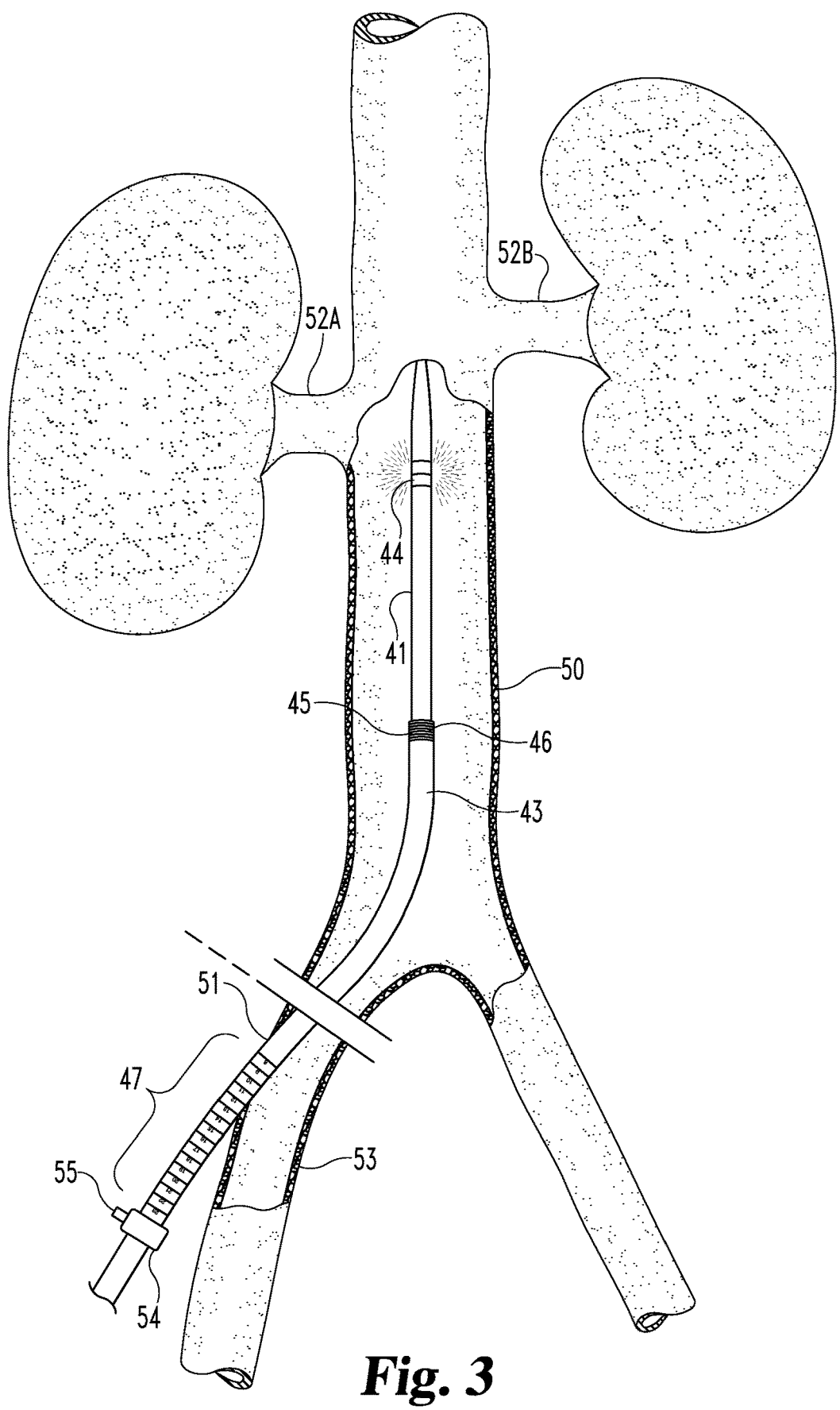
FIGS. 3-7 illustrate devices and steps used in certain embodiments for the delivery of a filter device.

The use of system 40 of FIG. 2 to deliver a vena cava filter to a patient will now be described with reference to FIGS. 3-7. FIG. 3 shows system 40 having been introduced into the vena cava 50 through a percutaneous access site 51 in the right femoral vein of a patient. Right renal vein 52A and left renal vein 52B feed into the vena cava 50, and in the illustrated embodiment it is desired to deploy a filter generally below the renal veins 52A and 52B, or "caudal" thereto. Depicted in FIG. 3 is dilator 41 advanced into vena cava 50 and at a position at which IVUS probe 44 can generate an image of at least the lowest-positioned renal vein, in most instances that being the right renal vein 52A. Prior to reaching this position, the IVUS probe 44 can be used to generate images of vascular landmarks distal to the renal veins, for example the right atrium, the hepatic veins, or other features. In certain embodiments the IVUS probe 44 will have a longitudinal resolution such that an image showing both renal veins 52A and 52B can be obtained. Sheath 43 is also percutaneously inserted into the vena cava, which insertion may have been before, with, or after that of dilator 41. The distal tip of sheath 43 is shown positioned well below the IVUS probe 44 so that it does not obscure IVUS probe 44 and thereby degrade generated image data. As can also be seen, the marking feature 47 includes at least portions remaining at skin level on the patient, and demarking the shaft distance from skin level to the distal tip of sheath 43. Further, in the illustrated embodiment, a repositionable scale marker 54 is positioned about sheath 43 and can be advanced to locations within marker feature 47. Scale marker 54 can include a stop or locking mechanism 55 which can be actuated to selectively release and secure the position of scale marker 54 along sheath 43. Any suitable mechanism can be used for this purpose including, for example, spring actuated friction stops against the sheath 43, tightenable screws or knobs which abut sheath 43 or cinch marker 54, or the like.

Figure 3B:
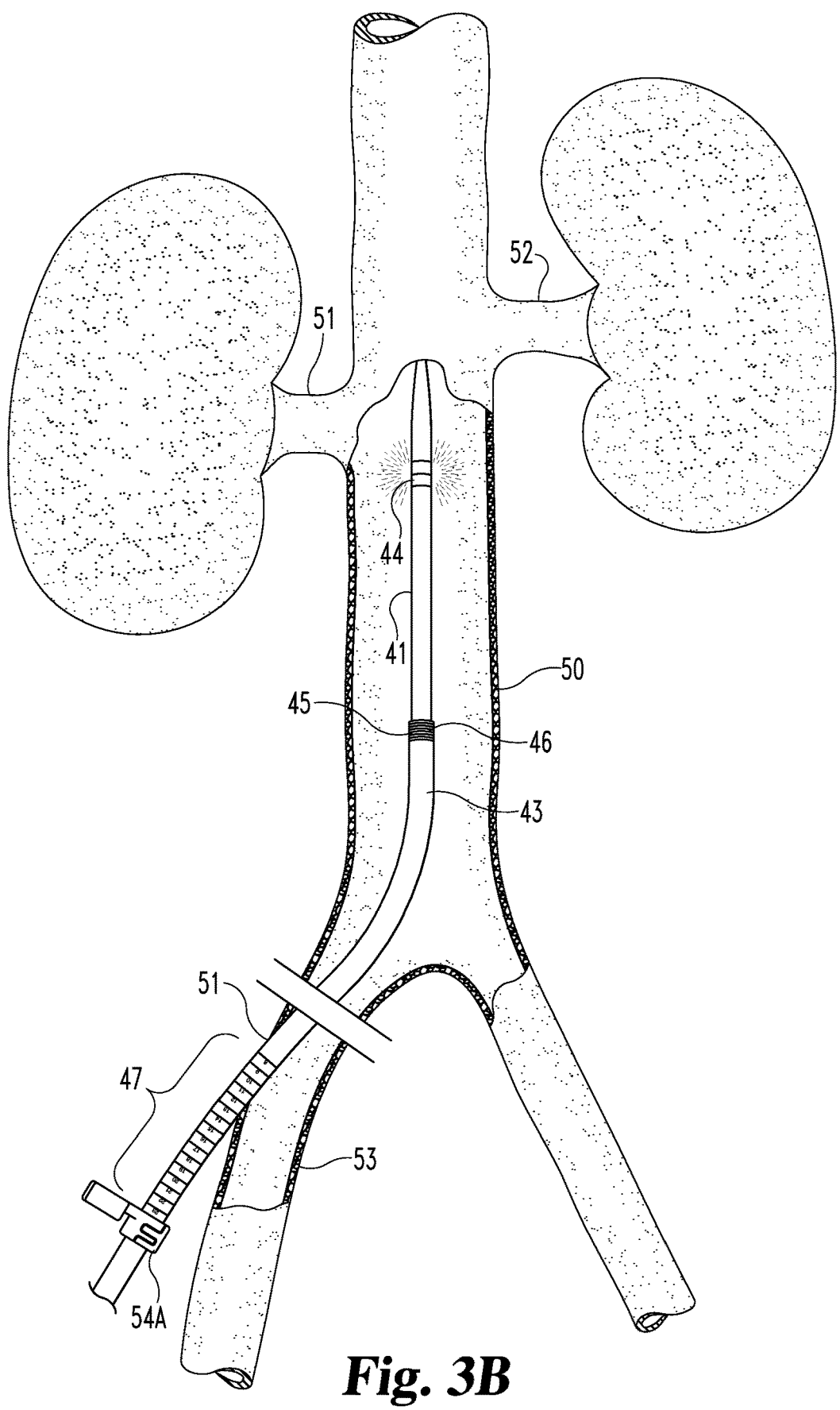
Figure 17:
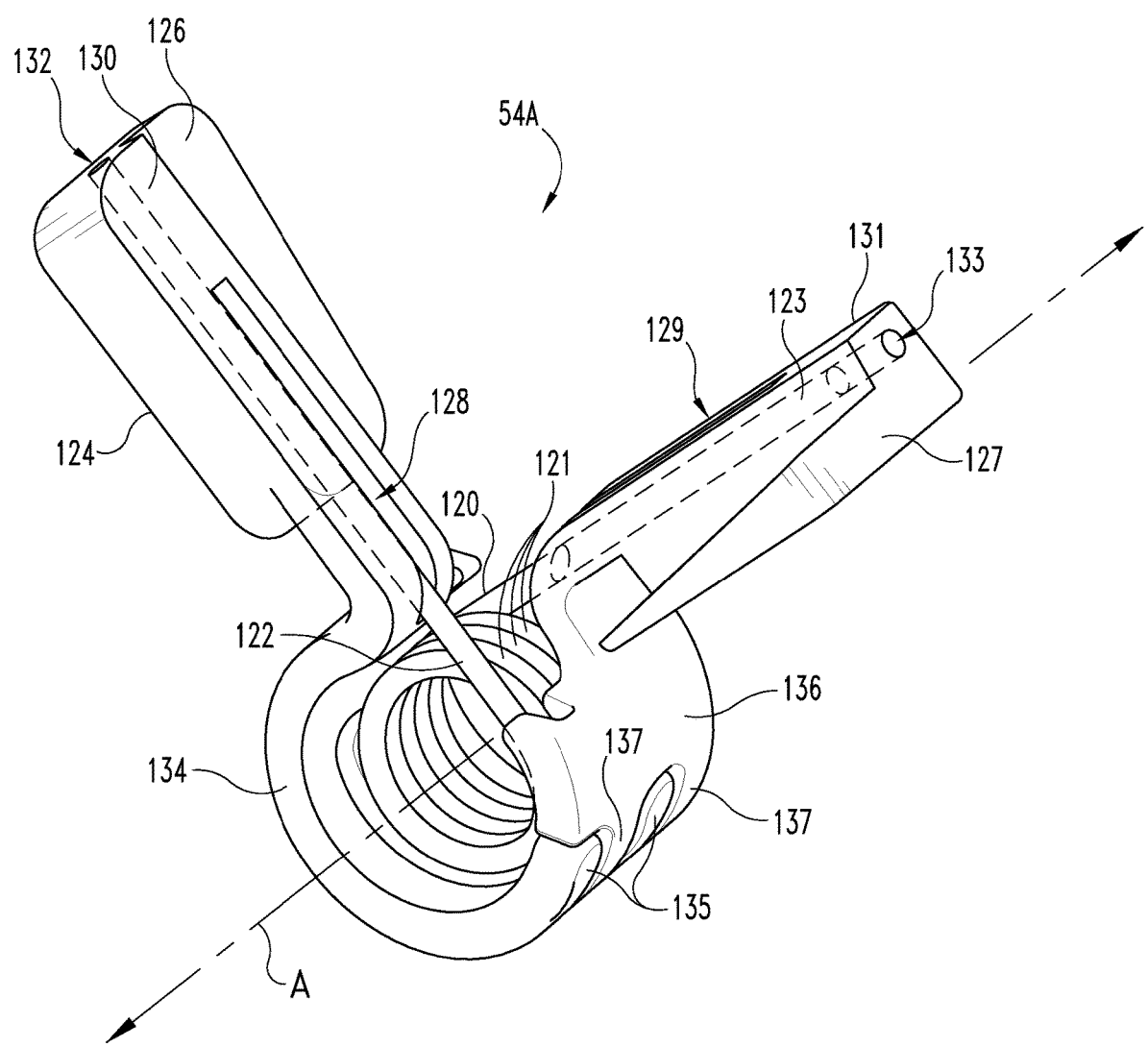
FIG. 17 provides a perspective view of a spring collar position marking device in accordance with one embodiment of the invention.

Referring to FIG. 17, the marker 54 can comprise a spring collar 54A, which itself represents another aspect of the invention, receivable around the sheath 43 (see illustrative FIG. 3B; it will be understood that spring collar 54A can also be used as marker 54 in other FIGs. in which marker 54 is shown). Spring collar 54A includes a wire spring 120 with a wire coiled to provide one or more wire loops and preferably a plurality of wire loops 121, which can be positioned adjacent to one another. Spring collar 54A can also include a first wire segment 122 extending from the wire loop(s) 121 and a second wire segment 123 extending from the wire loop(s) 121. In a relaxed (unstressed) condition, the segments 122 and 123 extend in directions that are radially offset from one another about a central axis "A" of the wire loop(s) 121, preferably at an offset of less than about 140 degrees about central axis "A". The spring collar 54A is configured such that the segments 122 and 123 can be moved radially toward one another, for example by squeezing them toward one another, to cause the internal diameter of the wire loop(s) 121 to increase in size in the resulting stressed condition of the spring collar 54A. In this fashion, spring collar 54A can be received around sheath 43 or another elongate, percutaneously introduced device, and can be sized to frictionally engage the outer surface of the sheath 43 or other device when in its relaxed condition or at least biasing toward its relaxed condition, and then frictionally disengage (or at least engage with less friction) when segments 122 and 123 are moved toward one another to increase the loop(s) diameter. This action can be used to facilitate repositioning the spring collar 54A along the sheath 43 or other device by disengaging, moving and then re-engaging the spring collar 54A. Other actions that reduce the diameter of loop(s) 121 may also be used, including for instance an action in which moving segments 122 and 123 toward one another causes such diameter to decrease while introducing stress into the spring collar. In such a design, for frictional engagement with the sheath 43 or other device, a feature for holding the segments 122 and 123 in position once the sheath/device is stressed and thereby engaged could be used, for example a clip or cap. The clip, cap or other feature could thereafter be removed or released to disengage the spring collar from the sheath 43/device, move the spring collar, and then re-applied after squeezing segments 122 and 123 toward one another to re-engage the sheath/device.

As illustrated in FIG. 17, the spring collar 54A can optionally include a molded plastic or other jacket attached to and that at least partially covers the wire spring 120. Such a jacket can be provided by one piece or optionally multiple pieces, and desirably includes at least tab portions connected respectively to each of the wire segments 122 and 123, with the tab portions providing a widened (relative to the diameters of the wire segments 122 and 123) area that can be used for manually gripping and manipulating the spring collar 54A for the engagement/disengagement operations discussed above. In the illustrated embodiment, the jacket includes a first jacket piece 124 and a second jacket piece 125. First and second jacket pieces 124,125 include respective tab portions 126,127 which define respective grooves 128,129 for receiving respective portions of wire segments 122,123. Grooves 128 and 129 terminate along the lengths of tab portions 126 and 127, and tab portions 126 and 127 include portions 130 and 131 outward of the grooves 128 and 129 which define respective apertures 132 and 133 for receiving outward end portions of the wire segments 122 and 123. If desired, a bonding agent can be applied within apertures 132 and 133 or at other locations to help to secure the jacket pieces 124 and 125 to the wire spring 120. Jacket pieces 124 and 125 can also include structures for jacketing the wire loop(s) 121 of the wire spring 120. With reference to first jacket piece 124, it includes a loop-covering portion 134 that includes one or more fingers 135, preferably two or more fingers. Second jacket piece 125 includes a loop covering portion 136 that includes one or more fingers 137, preferably two or more fingers. When jacket pieces 124 and 125 are assembled on the wire spring, finger(s) 135 and finger(s) 137 interleave but remain slidably disposed with respect to one another. In this fashion, when tab portions 126 and 127 are squeezed or otherwise forced toward one another to enlarge the loop(s) 121, finger(s) 135 and 137 will slide relative to one another so as to decrease their extent of interleaved overlap while still providing a structure that generally surrounds the loop(s) 121. Release of the tab portions 126 and 127 will then cause finger(s) 135 and 137 to slide again relative to one another so as to increase their extent of interleaved overlap while providing a loop(s)-surrounding structure. Jacket portions 124 and 125 can optionally each be monolithic pieces, as illustrated, providing both the respective tab portions and loop(s)-surrounding portions.

Figure 3C:
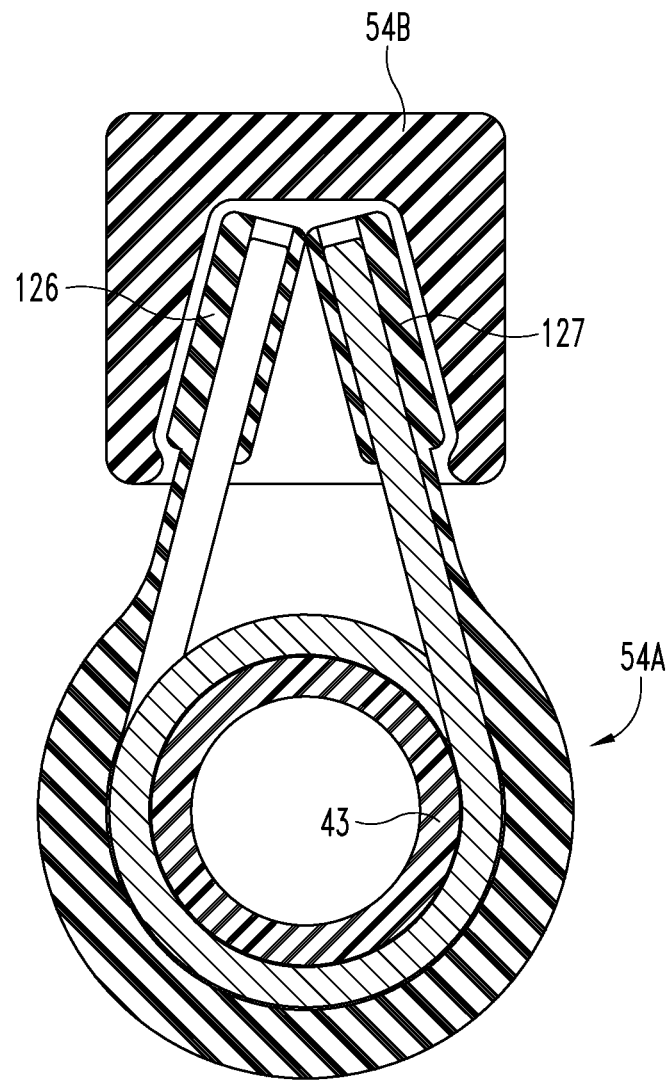

When the spring collar 54A or other scale marker 54 is frictionally engaged with the sheath 43 or other device, it can do so while compressing the sheath 43 or other device at a level which does not substantially deform the shape of the sheath 43 or other device (e.g. leaving open an internal lumen thereof) but which creates sufficient friction to resist movement of the collar 54A or other marker 54 along the sheath 43 or other device during use. For example, such friction can be sufficient to require a force of greater than 2 Newtons applied to the engaged collar 54A/marker 54 in the direction of the longitudinal axis of the sheath 43 or other device in order to cause sliding movement of the engaged collar 54A/marker 54, more preferably in the range of about 3 Newtons to 10 Newtons, and most preferably about 4 to about 5 Newtons. It will be understood that other force values could be utilized in varied circumstances depending for instance upon the particular percutaneously-introduced device and procedure requirements associated therewith. It will also be understood that the friction and resultant resistance to linear displacement of the engaged spring collar 54A or other marker 54 can depend, for instance, upon the extent of surface contact, the surface characteristics and materials of construction of the collar or marker and those of the sheath or other percutaneous device, which can also be varied in achieving the desired result. The variation of these and other parameters will be within the purview of those skilled in the field given the teachings herein. Moreover, as shown in FIG. 3C, in accordance with certain inventive embodiments, a spring collar 54A or other biased marker 54 can be equipped with a retainer device 54B that holds the collar 54A or other marker 54 in an unrelaxed (or stressed) condition when received around the sheath 43 or other device. For example, the sheath or other device can be packaged or handled with the collar 54A or other marker 54 received therearound, but equipped with the applied retainer device 54B to disengage or reduce compression of the sheath 43 or other device by the collar 54A or other marker 54. In this fashion, potential deformation of the sheath 43 or other device over time, e.g. during storage prior to use, can be reduced or eliminated. As illustrated, retainer device 54B can be a cap in which tab portions 126 and 127 are received and held closer together than they would be in a relaxed condition of the collar 54A, although other retainer elements or devices that resist return of the spring collar 54A to its relaxed condition could also be used.

Figure 4:
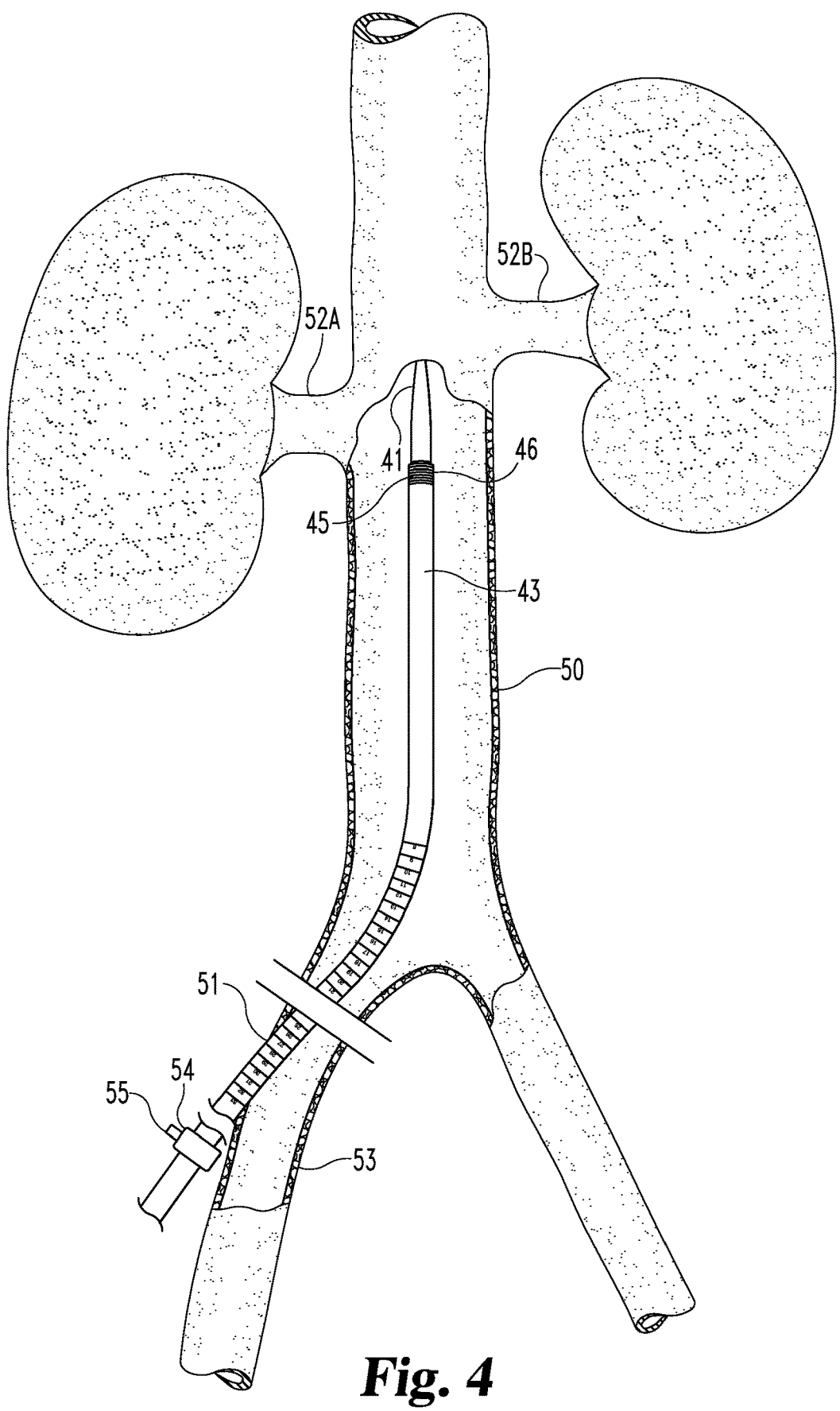

Returning to a discussion of an illustrative procedure, with particular reference to FIG. 4, while holding the position of IVUS probe 44 stationary, sheath 43 is advanced coaxially over dilator 41 until the distal tip of sheath 43 advances over IVUS probe 44. This event can be sensed tactilely as discussed above, and/or through a change in the image generated by IVUS probe 44 due to being covered by the wall of sheath 43 (potentially enhanced by the presence of echogenic marker 46, which can be configured to reflect ultrasonic energy sourced from the probe 44 within). At this point, the user knows that the distal tip of sheath 43 is positioned at the target position found with the IVUS probe 44. The user can then reference the scale markings within the marking feature 47 that coincide with the skin level of the percutaneous insertion site 51. A correlation can thereby be drawn between the positioning of the distal tip of the sheath 43 at the target site and a scale marking within marking feature 47. Again, in one embodiment, such scale marking includes a numeric value correlating to the distance from the marking to the distal tip of sheath 43. The repositionable scale marker 54, when present, can also be advanced and secured to abut the percutaneous insertion site 51 with the distal tip of sheath 43 at this target position. The dilator 41 and if still present the wire guide can then be removed from the sheath 43 while holding the sheath stably in position with the distal tip of the sheath 43 at the target position.

Figure 5:
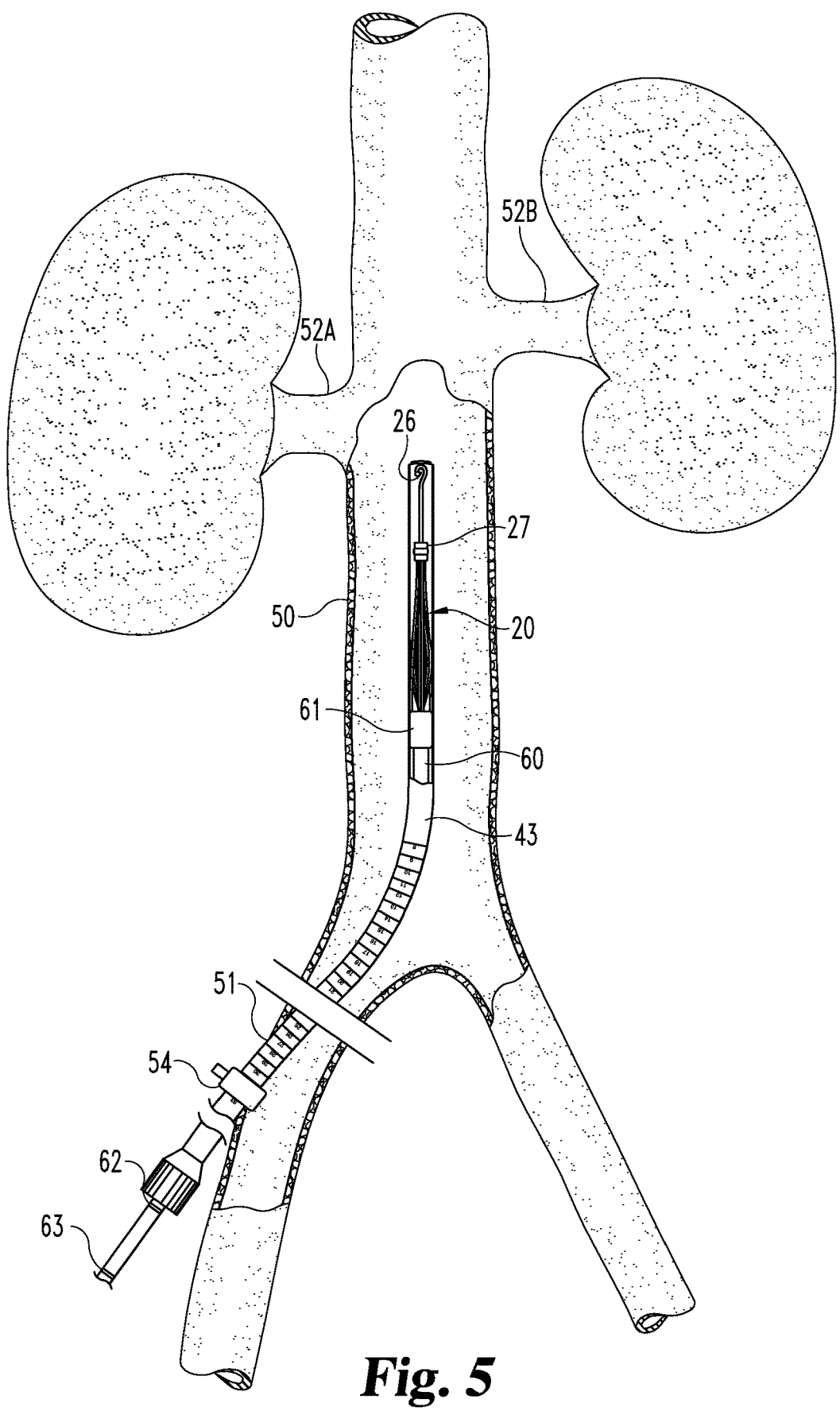
Figure 6:
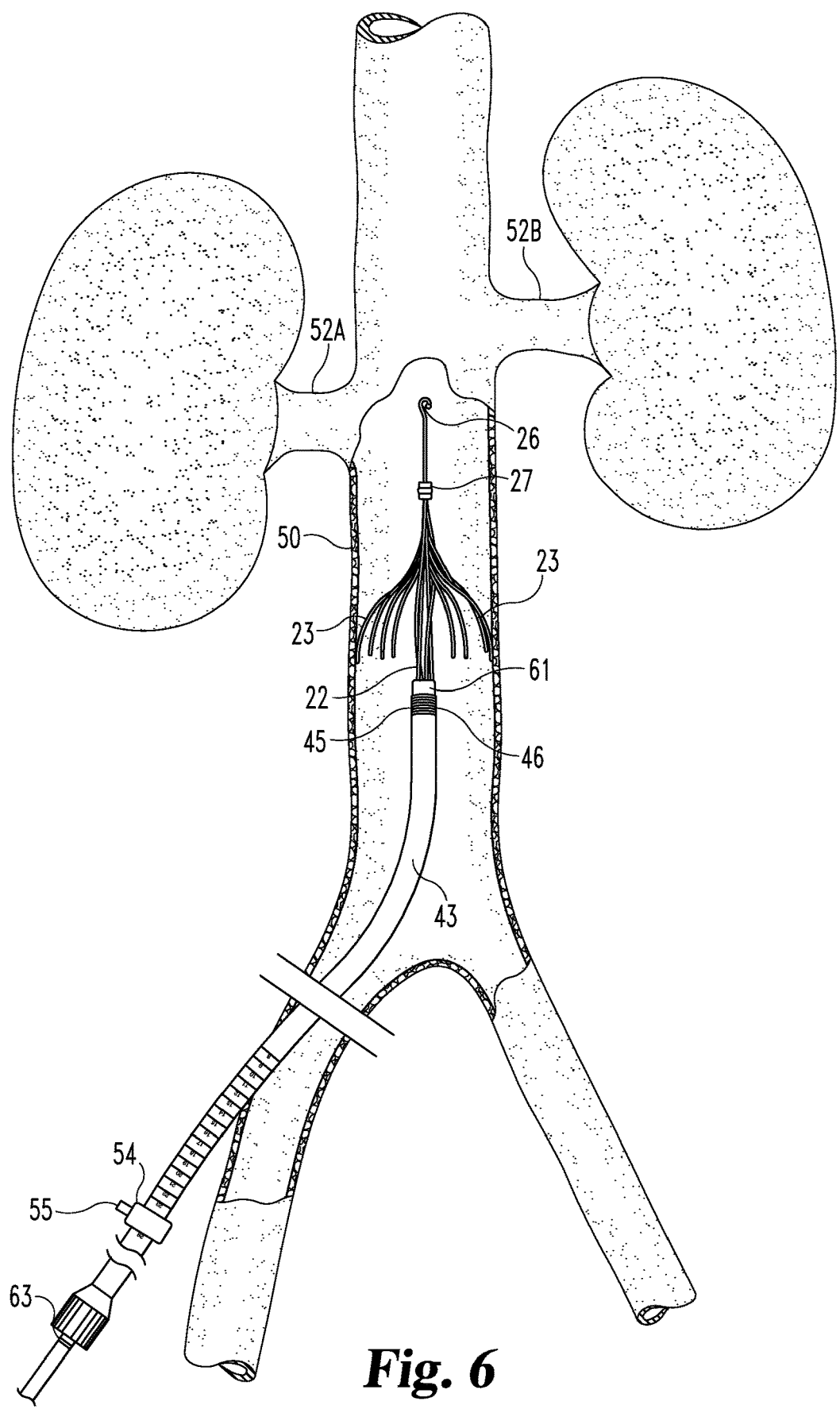

Referring now to FIGS. 5 and 6, thereafter, a filter introducer system carrying filter 20 (FIG. 1) is advanced into the sheath 43. In FIG. 5, shown is filter introducer system 60 advanced into sheath 43 to position the distal tip of filter 20 substantially at the distal tip of sheath 43. As noted above, this positioning can be discerned in any suitable manner. In the embodiment shown, filter introducer 60 includes proximal, visible markers 62 and 63 spaced longitudinally from one another, and positioned on introducer 60 so as to remain external of the patient during the procedure. When the distal-most marker 62 aligns with a distal-most portion of the sheath 43, or aligns with another identifiable reference associated with sheath 43, the distal tip of filter 20 is aligned with the distal tip of sheath 43.

With reference now to FIGS. 5 and 6 together, at this point, sheath 43 can be withdrawn until the proximal end of sheath 43 (or the associated reference point) is flush with marker 63, whereupon filter 20 is externalized from sheath 43 at the target location. In the illustrated embodiment, at this stage, the secondary legs 23 of filter 20 are deployed outwardly against the wall of the inferior vena cava 50; however, the primary struts 22 remain engaged by retaining element 61, such as a metal mount, located at the tip of introducer 60. Retaining device 61 is actuatable from a position external of the patient to release primary struts 22 of filter 20, for example by operating a button, switch, lever, or any other suitable mechanism. Such a mechanism is in use at present on the COOK® CLECT® filter set for femoral vein approach (William Cook Europe, Denmark), which mechanism can be used herein. Additionally, reference can be made to U.S. Pat. No. 5,324,304, which describes similar release mechanisms that can be used herein.

Figure 7:
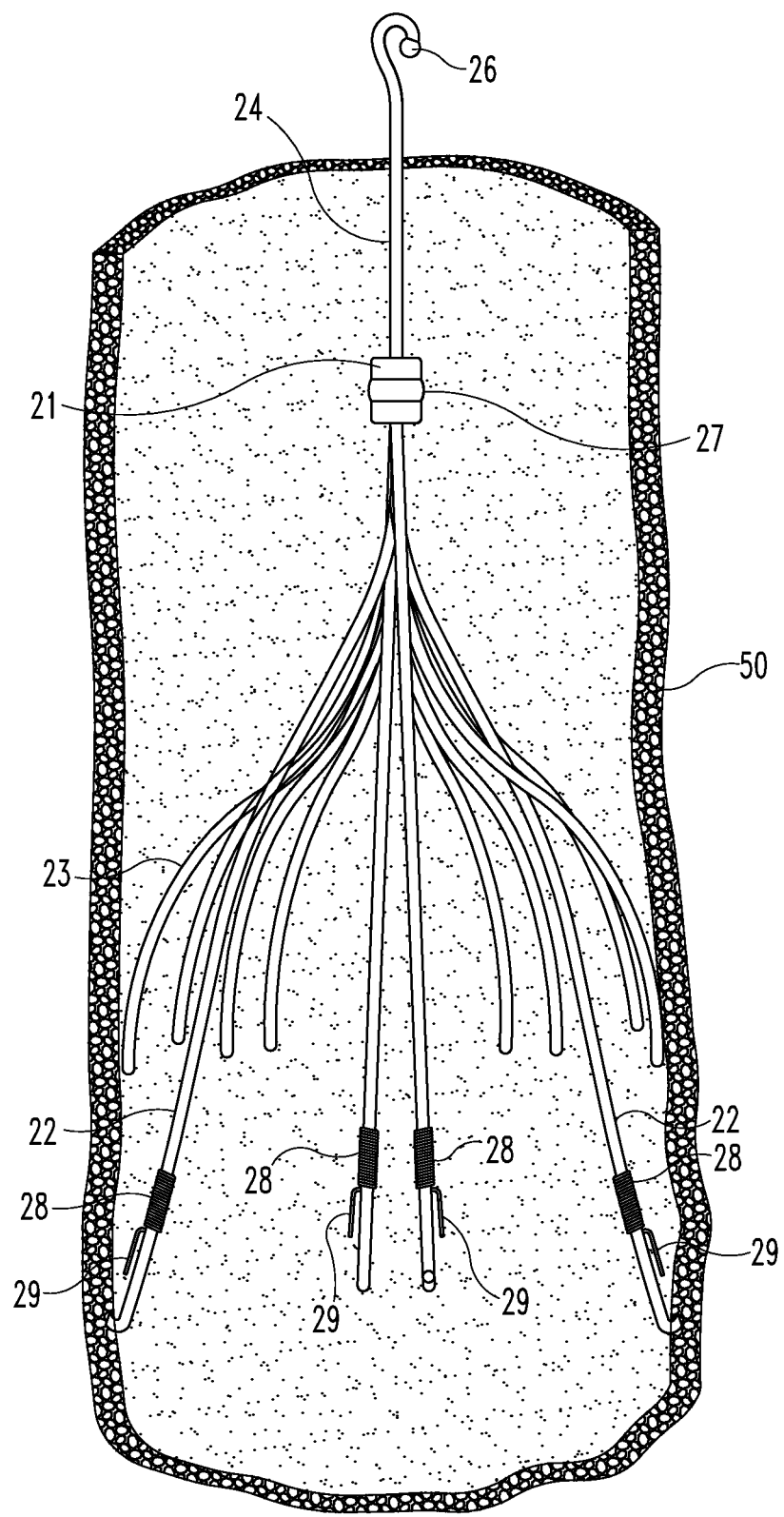

After release of the primary struts 22 from the retaining element 61, filter 20 fully deploys in vena cava 50, and sheath 43 and any other percutaneously introduced devices can thereafter be withdrawn from the patient. Shown in FIG. 7 is an enlarged view of filter 20 as deployed within the inferior vena cava 50, with both secondary struts 23 and primary struts 22 having expanded radially outwardly against the wall of vena cava 50. With filter device 20 so deployed, in certain embodiments the echogenic markers 26 and 27 are sufficiently spaced to be viewed by transabdominal ultrasound as distinct images. Still further, in desirable embodiments, echogenic markers 28 are located on primary struts 22 so as to be positioned against the caval or other vessel wall when in the expanded, deployed condition. The position of echogenic markers 28 and thus of the associated strut regions can thus be confirmed with ultrasound images. As noted above, the elongate generally straight filaments 29 extending from markers 28 can aid in the fixation of device 20 against the walls of vena cava 50 and/or can help to prevent migration of the struts 22 through the caval or other vessel wall.

Figure 16:
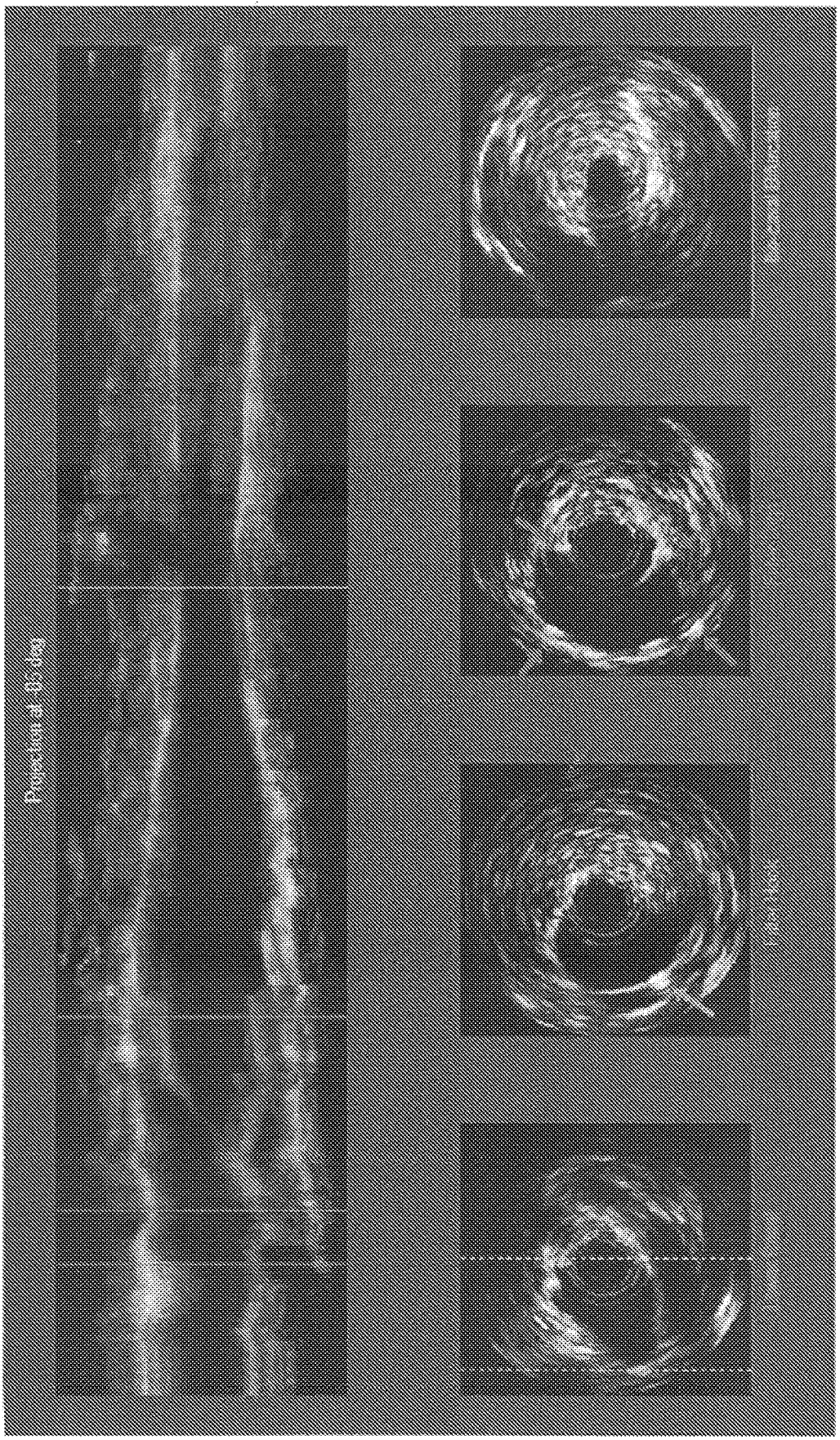
FIG. 16 provides illustrative IVUS-generated images useful for confirming the placement of a deployed filter device.

In advantageous operations, after deployment of the filter 20 from sheath 43 and release of the primary struts 22 from retaining device 61, the filter introducer 60 is withdrawn while leaving sheath 43 percutaneously inserted. The guide 42 can then be reinserted through sheath 43 and an IVUS-enabled catheter such as dilator 41 can be reintroduced over the guide 42. With the guide 42 extending into or beyond the filter 20, the IVUS-enabled dilator 41 can be advanced within vena cava 50 and the IVUS probe 44 can be used in the generation of images to confirm the deployment position of filter 20. In one mode, the IVUS images generated can be used to inspect the position of the primary struts 22 and/or secondary struts 23 against the wall of vena cava 50. To facilitate this inspection, echogenic markers (e.g. 28) positioned on struts 22 and/or 23 and configured to be apposed against the wall of vena cava 50 upon proper deployment of the filter 20 can be used to generate images from which such apposition can be confirmed or denied. The IVUS probe 44 can also if desired be advanced beyond filter 20 to generate an image of renal vein or veins 52A and/or 52B to confirm position of the filter 20 caudal thereto. After this inspection, and potentially also electronic storage of the confirming images for the patient record, the guide device 42 and IVUS-enabled dilator 41 can be withdrawn from the patient. For example, shown in FIG. 16 are images of a vena cava filter implanted in the vena cava of a sheep, obtained by advancing an IVUS-enabled catheter beyond the implanted filter and generating IVUS images during a pull-back of the catheter. Shown at the top is a projection image generated from a series of axial images, depicting the lower renal junction, the vena cava filter hook, the filter legs, and the ilio-caval bifurcation. The projection image has interpretive markings added by the user, in the form of color-coded vertical lines corresponding to anatomical landmarks and features of the implanted device. Desirably, the projection image or other IVUS-generated image(s) will depict the first and second ends of the device, which can optionally be marked on the image by the user. Shown at the bottom are axial IVUS images corresponding to the device features and anatomic landmarks discussed above and depicted in the projection image, and color coded to the vertical lines added to the projection image. These and other marking and/or indexing measures can be taken to add clarity to the interpretation of the image(s). Such an image or images can be obtained of an implanted vena cava filter or other vascular filter or other device, with accompanying physiologic landmarks from the patient, to confirm proper placement of the device following deployment. The optional presence of echogenic features on the device, e.g. on the filter hook and/or filter legs, can enhance the ability to visualize the device features in the confirming ultrasound images. The utilization of IVUS-generated device placement images to confirm the location of the implanted device after deployment, and for purposes of maintaining a patient medical record relating to the surgery, constitutes another embodiment of the invention and can be used in conjunction with any system or placement method described herein or otherwise. The collected IVUS data can be filtered to improve the IVUS image, for example by excluding data from certain segments or regions. For example, the projection image in FIG. 16 (top) was generated from data taken from the longitudinal volume depicted between the dotted lines in the left-most axial image found below. This technique and/or other filtering techniques can be used to improve the image quality given the teachings herein. The IVUS-generated images can be electronically stored in the patient record, e.g. using a data capture and storage system directly coupled to the IVUS device or system, or by otherwise transferring the electronic data to the patient record, and/or by retaining printouts or other "hard copy" version of the captured confirming images. In certain embodiments, the IVUS-generated image can serve as an alternative to any radiographic image (e.g. X-ray image) where no radiographic confirmation of placement is taken, and in other embodiments the IVUS-generated image can serve as an addition to a placement-confirming X-ray or other radiographic image in the patient record.

Figure 8:
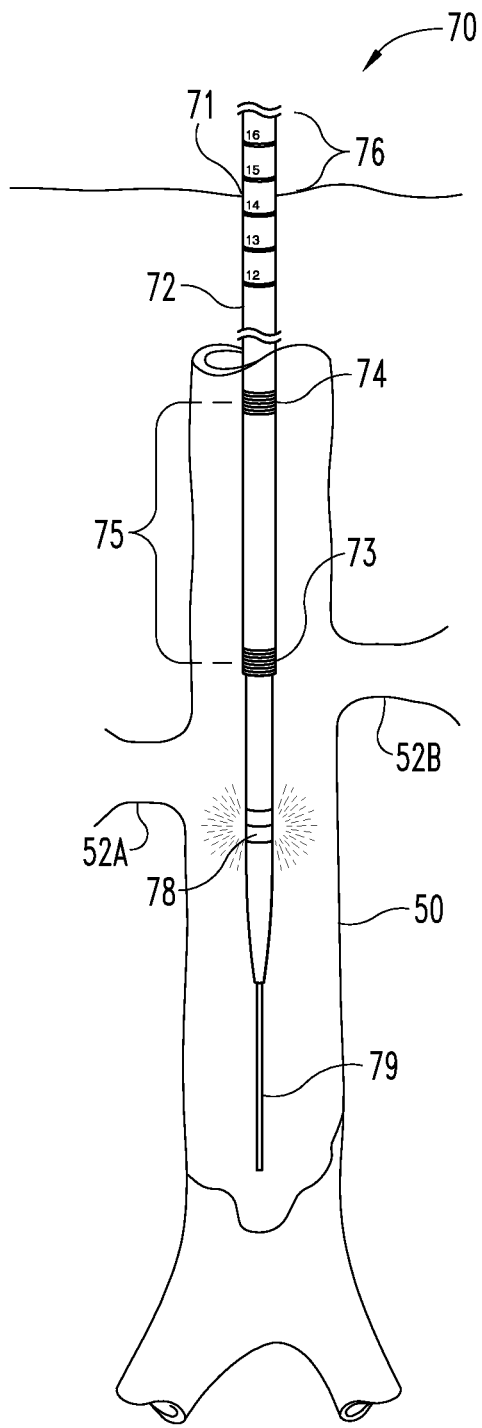
FIG. 8-10 illustrate devices and steps used in other embodiments for the delivery of a filter device.
Figure 9:
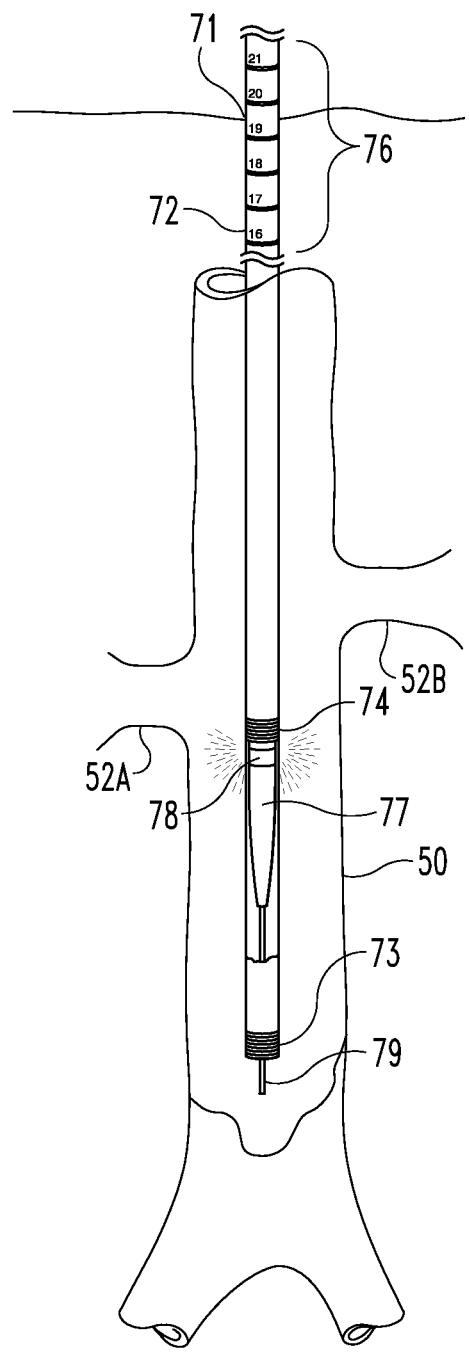

FIGS. 7-9 illustrate an embodiment of a delivery system for a vascular device, such as a vascular filter, that is useful from an approach descending downwardly within the vena cava, e.g. through a percutaneous access site in the left or right jugular vein. System 70 has numerous features which correspond directly with features of system 40 discussed above, to which reference can be made for details. System 70 includes an IVUS-enabled dilator having an IVUS probe 78, for percutaneous insertion through percutaneous access site 71. System 70 includes a sheath 72 translatable coaxially over the dilator. An echogenic marker 73 is provided at the distal end of sheath 72. Sheath 72 further includes an echogenic marker 74 spaced proximally of marker 73 a longitudinal distance 75. Markers 73 and 74 can optionally include physically discrete or physically integrated fluoroscopic markers as discussed above. Longitudinal distance 75 corresponds to a desired distance for advancement of the distal tip of sheath 72 beyond IVUS probe 78 to position the sheath for deployment of a vascular device, as discussed in further detail below. Sheath 72 also includes a marking feature 76 corresponding to marking feature 47 of sheath 43, desirably a numeric distance scale, as discussed above. It will be understood in this regard that the relative position of marking feature 76 along sheath 72 may differ from the position of marking feature 47 along sheath 43, due to the differing distances from the respective percutaneous entry sites the target site. System 70 also includes a guide device 79 such as a wire guide. Shown in FIG. 7 is the dilator with the IVUS probe 78 in position to image and identify a location at or just below the renal veins 52A and 52B which feed into inferior vena cava 50. This position is intended to be at or near the uppermost portion of the vascular implant when deployed. Sheath 72 is shown in FIG. 7 in position with its distal tip proximal of IVUS probe 78 for best viewing conditions.

Referring now particularly to FIG. 8, while holding the IVUS probe 78 in the target position, sheath 72 has been advanced along the dilator. In doing so, the advancement of the distal sheath tip over the IVUS probe 78 is recognizable by the user by a change in the generated IVUS image, which can be enhanced through the presence of an echogenic marker 73. As the sheath 72 is advanced further, the user will again note a change in the IVUS image as the more proximal echogenic marker 74 arrives overtop the IVUS probe 78. If desired, sheath 72 can be configured to also provide a tactile signal of this positioning. In this position, the distal tip of the sheath 72 has been advanced to a target location distal of the IVUS probe 78 from which pull-back of sheath 72 will be initiated for deployment of the implant. At this point also, the user can make visual reference to the visible marker feature 76 and in a particular embodiment to scale markings therein which align at skin level at the percutaneous entry site 71, or with any other suitable location correlating to the position of the distal tip of the sheath 72. While holding the sheath in position, potentially with continuing reference to the position of scale markings within the marking feature 76, the dilator including IVUS probe 78 and the guide 79 can then be withdrawn.

With reference now to FIG. 9, a filter introducer 80 carrying filter 20 can then be inserted through sheath 72. Filter 20 can for example be held by introducer 80 with a loop, hook or similar retaining device 84 located at the distal end of introducer 80 and engaging the hook of filter device 20. Similar to system 40 above, filter introducer 80 includes proximally-positioned external visible markers 82 and 83 spaced longitudinally along the shaft of device 80. The distal marker 82 aligns generally with a reference point, for instance the proximal end of sheath 72 or an element connected thereto, when the distal end of filter 20 is generally aligned with the distal tip of sheath 72. After advancing filter introducer 80 to this position while holding sheath 72 in place, sheath 72 can be withdrawn proximally until the distal end of sheath 72 (or piece associated therewith) is generally flush with marker 83, giving indication that the filter device 20 has been deployed from the distal opening of sheath 72. Retaining device 84 can then be actuated to release filter device 20 from introducer 80, thus leaving filter device 20 deployed within the inferior vena cava. Thereafter, if desired, the guide device 79 and the IVUS-enabled dilator can be re-introduced through sheath 72 and used to inspect the deployed filter 20 and the apposition of its struts against the caval wall. Echogenic markers 28 positioned on the primary struts 22 and/or the secondary struts 23 can facilitate capturing images showing those markers at or against the wall of vessel 50 to provide assurance that the filter 20 has properly and completely deployed. The guide 79, the dilator with IVUS probe 78 and if still present the sheath 72 can then be withdrawn from the patient.

Figure 11:
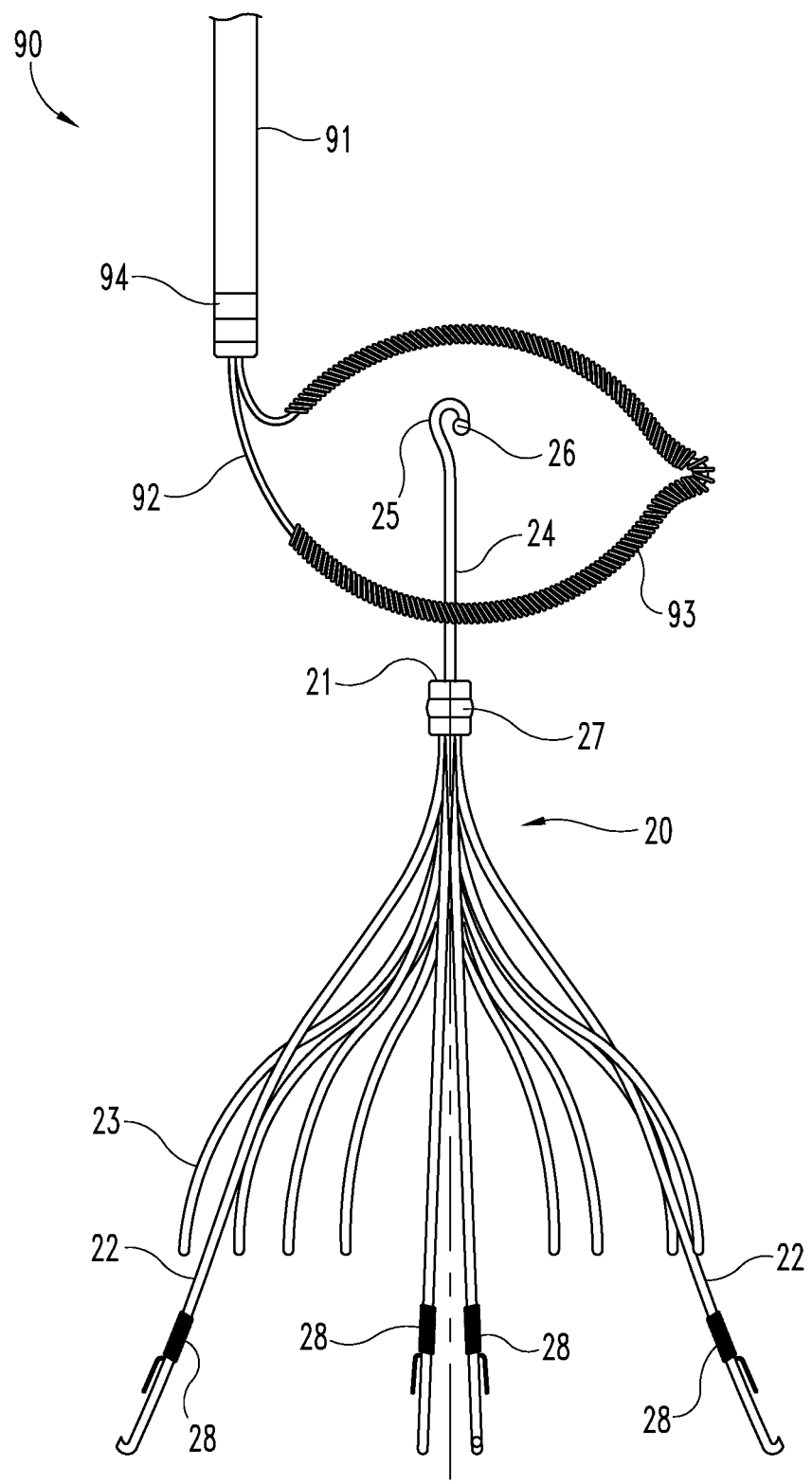
FIG. 11 provides a partial cut-away perspective view of one embodiment of an echogenically-marked vascular snare in position to capture a filter device.

In additional aspects of the invention, provided are IVUS-enabled and/or echogenically-marked percutaneously-insertable devices that can be used in the retrieval or delivery of vascular filters or other implant devices. FIG. 11 is a partial cut-away view of a percutaneous vascular snare device 90 embodiment of the invention. Vascular snare 90 includes an elongate shaft 91 having an internal lumen and a snare loop 92, for example made of a flexible filament(s) such as wire, which can be controllably deployed from and withdrawn into the lumen. Snare device 90 includes an echogenic marker 92 on at least a portion of the snare loop 92. Echogenic marker 92 can include a grooved structure, a coil such as a wire coil, a dimpled and/or grooved structure such as dimpled and/or grooved cannula, or any other suitable echogenic structure or material as discussed herein. Further, marker 92 can be mounted over the wire or other elongate filament forming the snare loop 92, or can be integrally formed into the wire or other elongate filament. Echogenic marker 92 is sized and configured to permit the deployment of the snare loop 92 smoothly out of and into the cannulated device 91 without substantial damage to either, so as to facilitate capturing devices with the snare. In certain embodiments, the snare device 90 includes an IVUS probe 94. The IVUS probe 94 can be used in obtaining ultrasound-generated images of a device to be captured and potentially retrieved with snare device 90. Still further, in some embodiments, the echogenic marker 93 of snare device 90 can be positioned on the snare loop 92, and the snare loop can deploy to a configuration, such that at least a portion of the marker 93 can be imaged using an ultrasonic signal generated with the IVUS probe 94. For these purposes, the snare loop 92 can deploy, at least in part, laterally from the lumen of the cannulated device 91, so as to position at least a portion of the echogenic marker 93, and potentially the entire marker 92, within the range of longitudinal resolution of the IVUS probe 94. In this manner, a user of snare device 90 can confirm deployment and position of the snare loop 92 in an open position by viewing images generated with IVUS probe 94. For these purposes, the snare loop 92 can be deploy to an open condition in which at least a portion of echogenic marker 93 aligns longitudinally with at least a portion of IVUS probe 94, or is longitudinally offset no more than about 3 mm therefrom. Echogenic marker 93 can, of course, also be visualized using an externally-generated (e.g. transabdominal) ultrasound image, to assist in guiding a capture or retrieval operation. Such external ultrasound imaging can also be used in conjunction with IVUS imaging derived from IVUS probe 94 in guiding the operation.

Figure 12:
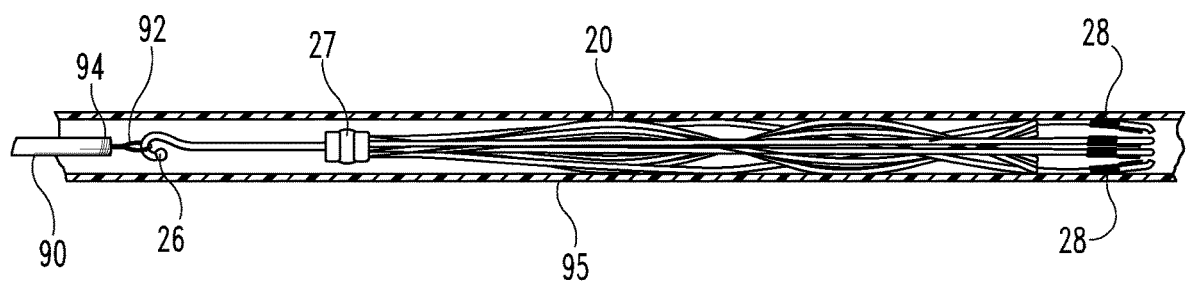
FIG. 12 provides a partial cut-away cross-sectional view of one embodiment of an echogenically-marked filter device within a retrieval sheath.

With continued reference to FIG. 11 and also to FIG. 12, in one mode, vascular snare 90 can be used to capture and retrieve an implanted vascular filter, for instance filter 20 described herein. External (e.g. transabdominal) ultrasound imaging can be used to discretely visualize echogenic markers 26 and 27 of filter 20 and echogenic marker 93 of snare device 20 (in an open condition) positioned therebetween and around neck 25 of filter 20. Snare loop 92 can then be closed by withdrawing it into the cannulated shaft 91 so as to capture filter 20, with the closed snare loop ultimately catching in hook 25. Alternatively or in addition, when IVUS probe 94 is present, vascular snare 90 can be used in generating an IVUS image to discretely and sequentially visualize marker 27 and marker 26 of filter 20, to guide positioning of the snare loop therebetween and around the neck 25 of the filter 20, whereupon it can be closed to capture the filter 20. After capture of the filter in the snare loop 92 in a closed condition, a cannulated retrieval device 95 (FIG. 12) such as a catheter or sheath can be advanced over device 91 and over filter 20 to force struts 23 and 22 radially inwardly to retrieve the filter 20 into the cannulated retrieval device 95. The snare 90, filter 20 and cannulated retrieval device 95 can then be removed from the patient. Alternatively, such a capture and/or retrieval operation can be used to reposition the filter 20 after deployment.

Figure 13:
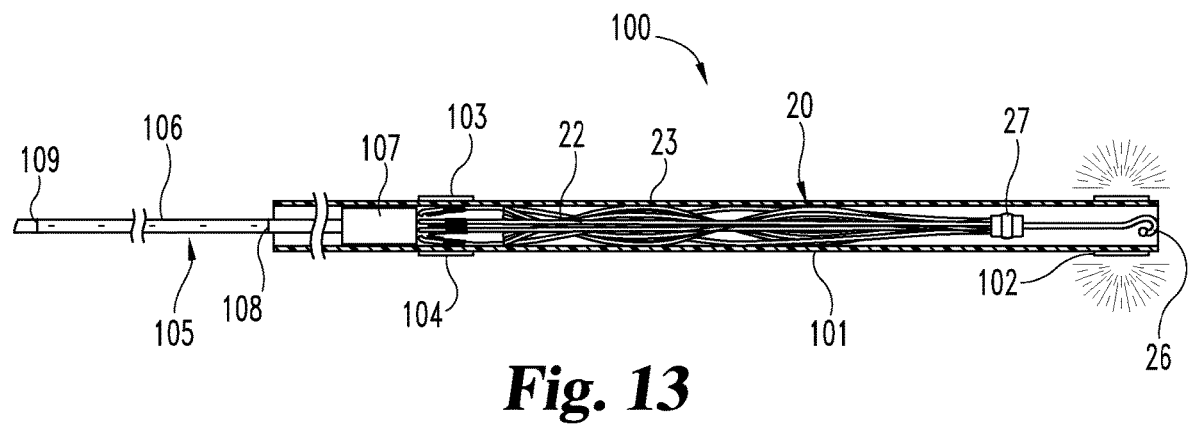
FIG. 13 provides a partial cut-away cross-sectional view of one embodiment of an IVUS-enabled filter delivery system.

FIG. 13 illustrates another embodiment of an IVUS-enabled filter delivery system 100 of the invention. System 100 includes a filter delivery sheath 101 with filter 20 housed in a lumen thereof. Delivery sheath 101 can have all of the attributes of sheath 43 discussed hereinabove, including but not limited to marking feature 47 and repositionable scale marker 54 (see, e.g., FIGS. 2-6). Delivery sheath 101 also has an IVUS probe 102 mounted proximate its distal tip. As discussed above, wire(s) and connectors for powering IVUS transducer element 102 and for transmitting signal data can be suitably routed along sheath 101 embedded within shaft walls, within additional lumens thereof, or properly positioned and protected, may share a lumen with filter 20. Any of these same arrangements or combinations thereof can be used for routing wire(s) and connectors for any of the IVUS probes disclosed herein. The presence of IVUS probe 102 on the implant delivery sheath 101 itself can eliminate the need to use a separate IVUS-enabled device (e.g., the IVUS-enabled dilator 41 discussed above), although in certain modes of use both types of IVUS-enabled devices could be used in guiding the device delivery.

Delivery sheath 101 also includes an echogenic marker 103 and/or a fluoroscopic marker 104. As discussed above, markers 103 and 104, when both present, can be provided by a single structure or material with dual function, or by separate pieces or structures. The arrangements discussed above can be suitably used. IVUS-enabled filter delivery system 100 also includes a filter introducer device 105, such as a catheter, having an elongate shaft 106 and a retaining element 107, such as a metal mount, in which the ends of primary struts 22 of filter 20 are received, and are releasably held. The ends of primary struts 22 can be released from retaining element 107 upon actuation of a button, switch or other suitable mechanism of introducer device 105, as discussed above for other embodiments.

Delivery sheath 101 can be used to percutaneously deliver vena cava filter 20 to a position generally as shown in FIGS. 3-6, with modification. To do so, sheath 101 can be percutaneously introduced (conventionally along with a dilator, which is then removed), e.g. through the right or left femoral vein, and advanced to a position to view the renal veins using the IVUS probe 102. With the position of the probe 102 generally at or caudal to the lower renal vein (typically the right), the position of the sheath 101 can be noted (e.g. using visible scale markings corresponding to feature 47 above). Holding the sheath 101 in place, the filter introducer 105 can be used to advance the hook of filter 20 to the distal tip of the sheath 101, for example using alignment of external, visible proximal marker 108 on introducer 105 with a feature on or associated with sheath 101 to signal that the distal tip of filter 20 is aligned with the distal tip of sheath 101. The position of the distal tip of sheath 101 within the inferior vena cava can then be confirmed using the external (e.g. skin-level) visible scale markings on the sheath and/or using the IVUS probe 102 to visualize the renal vein(s) again. The sheath can then be pulled back to align the feature on or associated with sheath 101 with external, visible marker 109 to signal that filter 20 has been deployed from the distal opening of sheath 101. The release actuator for retention device 107 can then be operated to release primary struts 22 of filter 20 to fully deploy the filter 20.

Figure 14:
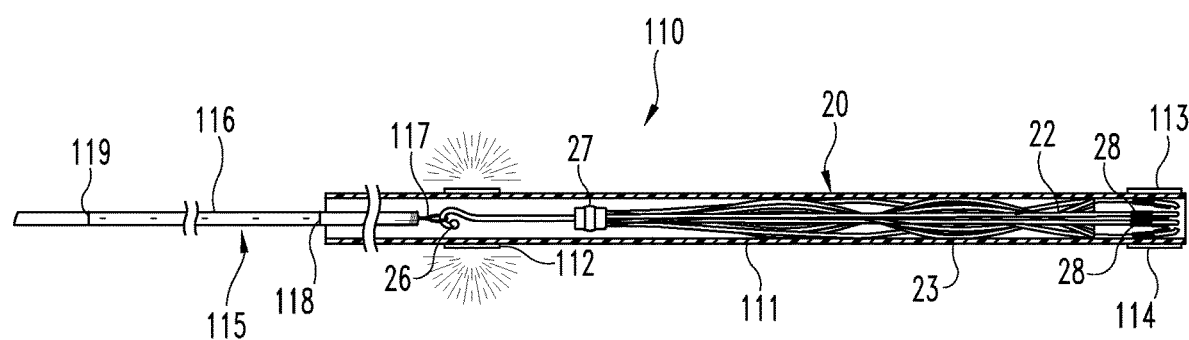
FIG. 14 provides a partial cut-away cross-sectional view of another embodiment of an IVUS-enabled filter delivery system.

FIG. 14 illustrates still another embodiment of an IVUS-enabled filter delivery system 110 of the invention. System 110 includes a filter delivery sheath 111 with filter 20 housed in a lumen thereof. Delivery sheath 111 can have all of the attributes of sheaths discussed hereinabove, including but not limited to external visible marking features (e.g. 76, FIGS. 8-10) and a repositionable scale marker (e.g. 54, FIGS. 2-6). Delivery sheath 111 also has an IVUS probe 112 a distance proximal to its distal tip. The presence of IVUS probe 112 on the implant delivery sheath 111 itself can eliminate the need to use a separate IVUS-enabled device (e.g., an IVUS-enabled dilator as discussed above), although in certain modes of use both types of IVUS-enabled devices could be used in guiding the device delivery.

Delivery sheath 111 also includes an echogenic marker 113 and/or a fluoroscopic marker 114 proximate its distal tip, the construction of which can be as discussed hereinabove. System 110 also includes a filter introducer device 115, such as a catheter, having an elongate shaft 116 and a retaining element 117, such as a hook, releasably engaging the hook of filter 20. The hook of filter 20 can be released from retaining element 117 upon actuation of a button, switch or other suitable mechanism of introducer device 115, as discussed above for other embodiments.

Figure 10:
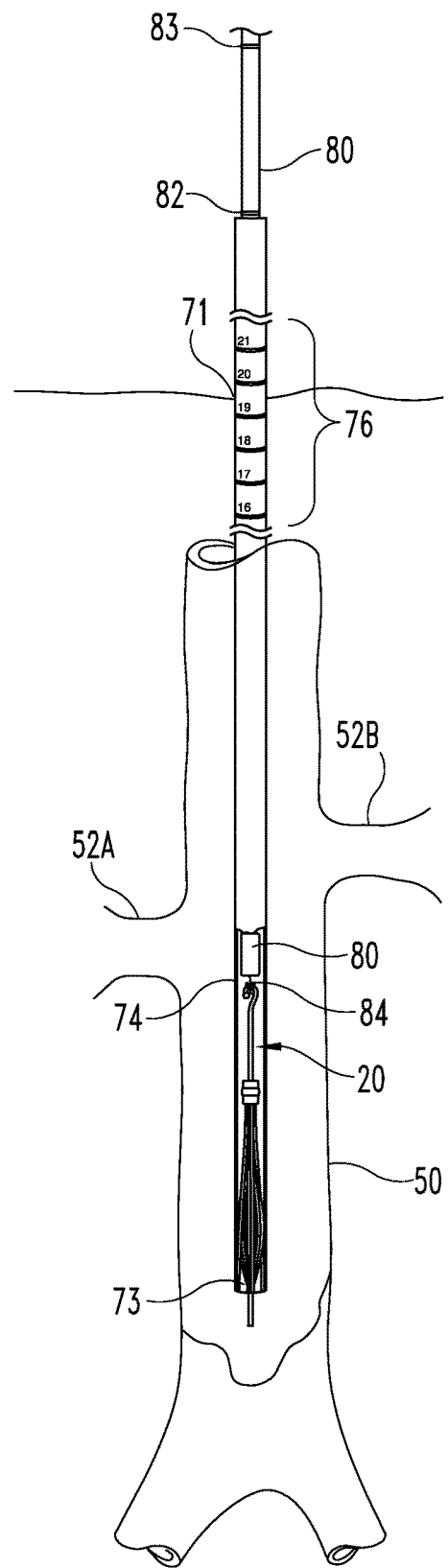

Delivery sheath 111 can be used to percutaneously deliver vena cava filter 20 to a position generally as shown in FIGS. 8-10, with modification. To do so, sheath 111 can be percutaneously introduced (conventionally along with a dilator, which is then removed), e.g. through the right or left jugular vein, and advanced to a position to view the renal veins using the IVUS probe 112. With the position of the probe 112 generally at or caudal to the lower renal vein (typically the right), the position of the sheath 111 can be noted (e.g. using external visible scale markings corresponding to features 47 or 76 above). Due to the distance between IVUS probe 112 and the distal end of sheath, this position will place the distal end of sheath 111 well caudal the renal vein(s), at a position corresponding to the desired lowermost point of the deployed filter implant. In the illustrated embodiment, the distance from IVUS probe 112 to the distal sheath tip is approximately equal to or slightly greater than (e.g. up to about 130% of) the length of filter 20 when deployed. Holding the sheath 111 in place, the filter introducer 115 can be used to advance the distal leg ends of filter 20 to the distal tip of the sheath 111, for example using alignment of external, visible proximal marker 118 with a feature on or associated with sheath 111 to signal that the distal tip of filter 20 is aligned with the distal tip of sheath 111. The position of the distal tip of sheath 111 within the inferior vena cava can then be confirmed using the external (e.g. skin-level) visible scale markings on the sheath and/or using the IVUS probe 112 to again visualize the renal vein(s). The sheath can then be pulled back to align a feature on or associated with sheath 111 with external, visible marker 119 to signal that filter 20 has been deployed from the distal opening of sheath 111. The release actuator for retention device 117 can then be operated to release the hook 25 of filter 20 to fully deploy the filter 20.

In additional embodiments, unique ultrasound image guidance methods and systems are provided. These methods and systems can be used in conjunction with implant devices and delivery/retrieval components discussed hereinabove, or with other devices or components. In one aspect, ultrasound guidance of percutaneous procedures can be provided using a combination of real time IVUS images and electronically-stored images. The electronically-stored images can, for example, be sequential images of a vessel acquired during pull-back of an IVUS probe (e.g., on IVUS-enabled dilators, sheaths or snares as discussed above) within the vessel, desirably at a constant speed, or generated images reconstructed from a plurality of such sequential images. Constant-speed pull-back devices for these purposes are known and commercially available. The generated, stored images can for example be three-dimensional or two-dimensional images of the length of vessel in which an implant such as a filter is to be deployed, reconstructed from a plurality of sequential, cross-sectional or otherwise segmental images of the vessel.

Figure 15:
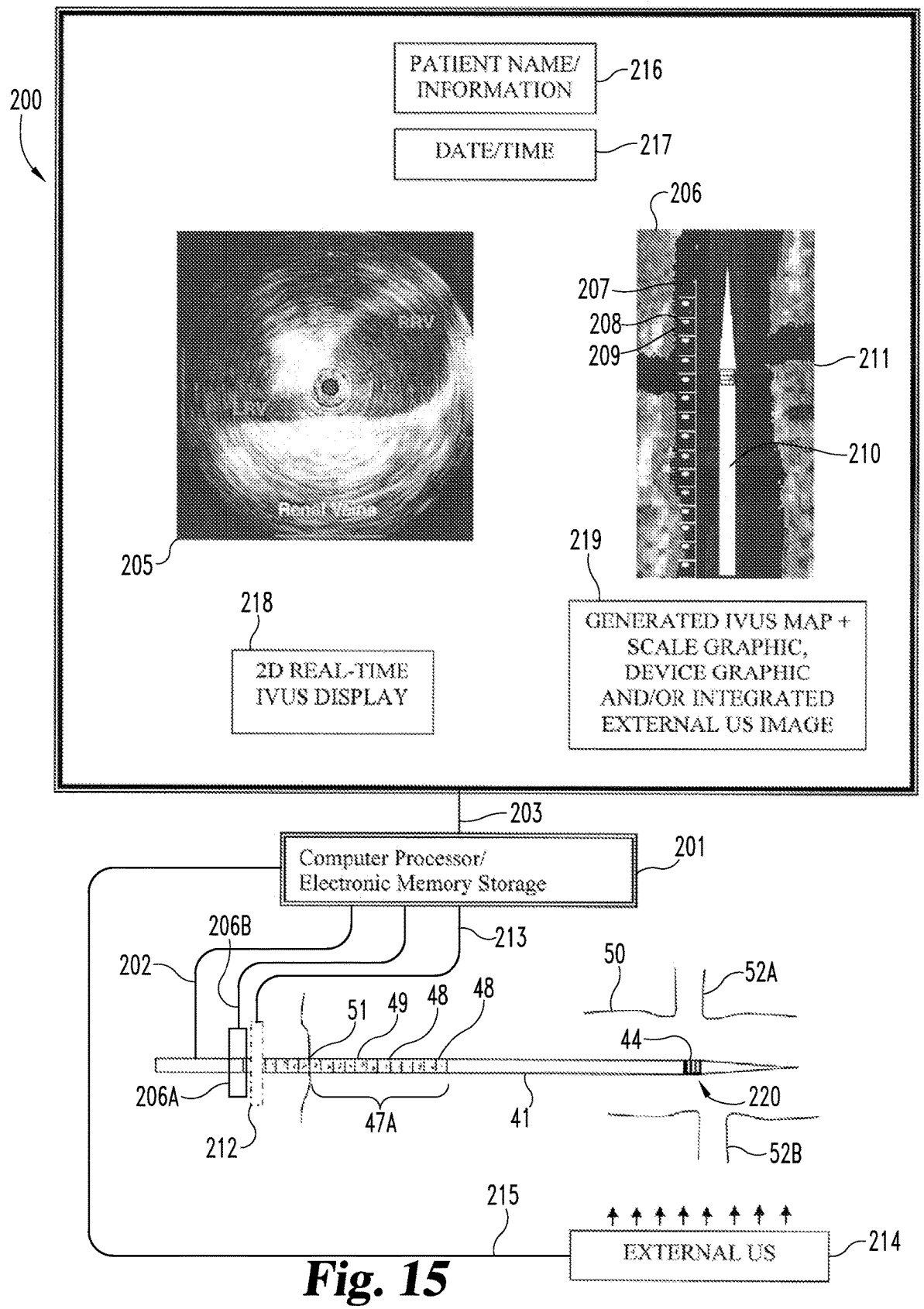
FIG. 15 provides a schematic representation of an image-guided medical device delivery system.

With reference to FIG. 15, provided is a schematic showing components of one embodiment of such a system. System 200 as depicted includes IVUS-enabled dilator 41 as described above (FIGS. 2-4), although other IVUS-enabled devices such as the dilator of FIGS. 8-9, snare 94 (FIG. 11) or delivery sheaths 101 (FIG. 13) or 111 (FIG. 14) can be substituted for dilator 41. Dilator 41 includes IVUS probe 44 and also includes a marking feature 47A, which can be the same as marking feature 47 discussed hereinabove in connection with FIGS. 2-6) and thus include individual scale markings 48 denoting a distance from the marking to a distal feature of dilator 41, such as the distance from the individual scale marking to the IVUS probe 44, and associated numerical markings 49. Dilator is shown percutaneously inserted with scaled regions of marking feature 47A occurring at skin level at entry site 51 on the patient.

System 200 includes a computer processor 201, which can also include an electronic memory storage for storing data and images. Computer processor 201 receives signal data from IVUS probe 44 via data transmission connection 202, which can for example be a wired or wireless connection. Computer processor 201 generates ultrasound images of vessel 50 using the transmitted signal data. Processer 201 is electronically connected via connection 203 to a visual display device 204 such as a display monitor. Display device 204 displays two-dimensional, real time IVUS images 205 generated using IVUS probe 44. In the depicted image 205, shown are the left and right renal veins generated by IVUS probe 44 positioned closely thereby. Display device 204 also displays an image 206 generated by reconstructing a plurality of previously-acquired two-dimensional, cross-sectional image data sets from IVUS probe 44. Algorithms for these purposes are known and are also available in commercially available IVUS devices and associated software, including those available from Volcano Corporation (San Diego, CA, USA). The previously-acquired data sets for reconstructing image 206 can be obtained during a pull-back of dilator 41, desirably at constant speed, during which IVUS image data are collected, desirably at regular time intervals. A pull-back device 206A can be used for these purposes, embodiments of which are also commercially available from Volcano Corporation.

In one embodiment, a graphical scale 207 is displayed on or in conjunction with image 206. Scale 207 can have scale markings 208 which correlate to individual scale markings 48 on dilator 41. Scale 207 can also have respective associated numerical markings 209 which correlate to respective associated numerical markings 49 on dilator 41. Thus, for example, a scaled marker on graphical scale 207 that is numbered "10 cm" will align longitudinally on or next to image 206 at a point correlated to the longitudinal position of IVUS probe 44 when a corresponding "10 cm" scaled marker of marking feature 47A occurs at skin level of entry site 51. Reliable external reference points for marking feature 47A other than skin level could also be used. In one manner of generating and locating graphical scale 207, at the starting point for pull-back, a user can input to the processor 201 the numeric indicia 49 having associated marker 28 at skin level. Using time-elapsed and constant-speed information provided to processor 201 by pull-back device 206A via connection 206B, processor 201 can ascertain how far probe 44 has traveled when generating a given image data set to be incorporated in the reconstruction of image 206, and can thereby accurately generate scale 207 in reference to the reconstructed image 206. In other modes of accurately generating scale 207, pull-back device 206A can include a device for directly measuring the distance traveled by dilator 41 during the pull-back, for example by detecting revolutions of a roller wheel of known circumference, or any other suitable means, and can communicate traveled distances to processor 201 that correlate to images acquired. Alternatively, such a direct measuring device can be provided in a separate position-tracking device 212 which communicates similar information to processor 201 concerning dilator 41 shaft travel distance during image acquisition via connection 213. As another alternative, during pull-back, a user can manually communicate shaft travel increments to processor 201 during image capture while watching marking feature 47A as it moves past skin level or another reference point. These or other measures for accurately associating scale 207 with image 206 can be used.

In certain embodiments, a graphical image 210 having features generally correlating to those of dilator 41 or the other device in use is displayed in association with image 206, potentially also in combination with scale 207. The graphical image 210 can include a graphical representation 211 of the IVUS probe 44, the distal tip of the device in use, and/or other device features. The position and movement of the image 210 relative to image 206 can be correlated to the position of dilator 41 (or the other device in use) within the vessel 50. This can be accomplished by inputting to processor 201 information related to shaft travel of dilator 41 during the procedure, starting from a known reference point which may for example be manually inputted by a user based upon visual observation of marking feature 47A relative to skin level or another reference point, and/or may be a direct continuation of the above-described positional tracking of the device 41 during the pull-back/image acquisition phase, for which the original positional input information from the user at the start of pull-back may continue to serve as a known reference point. To track shaft travel, devices for directly measuring shaft travel (e.g. as a part of the pull-back device 206A or a separate position-tracking device 23), or manual entry by a user, can be used, as discussed above.

In a different mode, sequential images that continue to be acquired by IVUS probe 41 during the procedure can be compared, using an appropriate algorithm and processor 201, to prior-acquired images obtained to generate image 206. The newly-acquired images can then be registered to prior-acquired images of known position along image 206, and the graphical image 210 can be positioned accordingly, e.g. by aligning graphical IVUS probe image 211 with the registered prior-acquired image.

System 200 can also include an external ultrasound imaging probe 214 (e.g. a transabdominal probe) connected to processor 201 via transmission connection 215. Alternatively or in addition to graphical images 207 and/or 210 discussed above, real-time external ultrasound images can be positionally registered to prior-acquired and generated IVUS image 206 and displayed therein or adjacent thereto, via appropriate fiduciary points established during the generation of IVUS image 206, for example by fixing the position of probe 214 during the procedure and acquiring fiduciary points during the pull-back operation, such as the location of the starting and finishing positions of an externally-imaged echogenic marker (e.g. 45, FIG. 2) respectively at the start and end of the pull-back to generate image 206. In this manner, historic IVUS data and real time external ultrasound data can be together used to guide a device delivery or retrieval operation. Of course, real-time IVUS data and images can also be used in conjunction with the historic IVUS data and real time external ultrasound data.

The display 204 can also include patient-specific information 216 and date/time information 217, as well as appropriate image descriptors 218 and 219, or other standard system performance or setting information.

In still further embodiments of the invention, systems and methods as described above which employ an ultrasound-emitting IVUS probe on a percutaneously-introduced device, can be used in conjunction with an external (e.g. transabdominal) ultrasound unit that is tuned to receive an ultrasound signal from the IVUS probe, and thereby detect the location of the IVUS probe as an "active" ultrasound marker in the system, or detect the location of a separate echogenic marker(s) on the introduced IVUS device or neighboring devices based upon the reflection by the separate marker(s) of the internally-generated IVUS signal. In this fashion the relative location of portions of the introduced device(s) can be detected with external ultrasound based on the IVUS-probe-generated, and potentially reflected, ultrasound signal. In addition or alternatively, the internally-generated IVUS probe signal can be received by the external ultrasound unit and processed to develop images of biological structures, thus providing an "inside out" ultrasound image generation system. In some embodiments, the external receipt and processing of the signals from the IVUS probe can be accomplished using an external ultrasound unit also used simultaneously or intermittently to emit and detect reflected ultrasound for development of ultrasound images, as discussed hereinabove. Alternatively, separate external ultrasound units can be used, one tuned to detect the IVUS probe-generated signals, and one functioning to generate images of biological structures and potentially other features of the introduced device from externally-generated ultrasound. In certain modes of practice, images or corresponding signals generated from both ultrasound emitted by the internal IVUS probe and by an external unit can be used together, either displayed as separate images to a user or processed and combined using an algorithm (e.g. with registration) to generate a single, enhanced image for display. Such processing can be achieved using a computer processor as described herein. Systems and methods as here described having images developed using IVUS probe-generated ultrasound that is detected externally, alone or in combination with externally-generated ultrasound, form additional embodiments of the invention whether used with the specific systems described in conjunction with the drawings above, or otherwise.

It will be understood that although embodiments described herein are at times discussed in connection with the delivery of, or features of, a vascular filter and related sheath and/or catheter deployment devices, embodiments of the invention can likewise involve the delivery of, and features of, other percutaneously-deliverable vascular devices such as stents, stent valves, occluders, embolization devices, anastomosis devices, and the like. These and other permutations will be within the purview of those of ordinary skill in the art given the teachings herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

The invention claimed is:

1. A system for ultrasound guidance, comprising:
   a computer processor for receiving signal data from an intravascular ultrasound probe mounted on an elongate percutaneously introducible device having a distal tip located distally of the intravascular ultrasound probe and generating ultrasound images using the signal data, wherein the intravascular ultrasound probe travels correspondingly with the elongate percutaneously introducible device;
   a visual display device electronically connected to the computer processor; and
   said computer processor and display device configured to display on the visual display device two-dimensional, real time images generated by the computer processor using the signal data simultaneously with and spaced from a three-dimensional image generated from prior-acquired intravascular ultrasound image signal data from the intravascular ultrasound probe, and wherein the computer processor and visual display device are configured to display within the three-dimensional image on the visual display a graphical image representing a position of the intravascular ultrasound probe, and wherein the computer processor is configured to perform a comparison of the two-dimensional, real time images to the prior-acquired intravascular ultrasound image signal data and to position the graphical image within the three-dimensional image based on the comparison, wherein the computer processor and visual display device are configured to display on the visual display device a reference scale, wherein the reference scale is generated from the prior-acquired three-dimensional ultrasound image and is correlated to the real time two-dimensional image.

2. The system of claim 1, wherein the three-dimensional image is generated by reconstructing a plurality of previously-acquired two-dimensional, cross-sectional image data sets from the intravascular ultrasound probe.

3. The system of claim 1, also including the elongate percutaneously introducible device.

4. The system of claim 1, arranged wherein the computer processor receives the signal data via a wired data transmission connection.

5. The system of claim 1, arranged wherein the computer processor receives the signal data via a wireless data transmission connection.

6. The system of claim 1, wherein the visual display device comprises a display monitor.

7. The system of claim 3, wherein the elongate percutaneously introducible device is a dilator.

8. The system of claim 1, wherein the prior-acquired intravascular ultrasound image signal data comprises position-tracking data correlated to image data.

9. The system of claim 1, wherein the computer processor is configured to compare the two-dimensional, real time images to the prior-acquired intravascular ultrasound image signal data in order to at least one of (i) position the at least one of a reference scale and a graphical image and (ii) adjust the at least one of a reference scale and a graphical image.

10. The system of claim 1, also comprising an external ultrasound imaging probe connected to the computer processor.

11. The system of claim 10, wherein the computer processor and display device are configured to display real-time external ultrasound images positionally registered to the three-dimensional image.

12. The system of claim 10, wherein the external ultrasound imaging probe is tuned to receive an ultrasound signal from the intravascular ultrasound probe.

13. The system of claim 12, also comprising a second external ultrasound imaging probe.

14. The system of claim 1, for ultrasound guidance of the delivery of a percutaneously-deliverable vascular device, the system also comprising:
   the elongate percutaneously introducible device;
   a delivery catheter; and
   a percutaneously-deliverable vascular device received in the delivery catheter.

15. The system of claim 14, wherein the percutaneously-deliverable vascular device is a filter, stent, stent valve, occluder, embolization device, or anastomosis device.

16. The system of claim 1, also comprising the elongate percutaneously introducible device, and wherein the elongate percutaneously introducible device is a delivery sheath carrying a percutaneously deliverable vascular device configured for deployment from a distal opening at the distal tip of the delivery sheath.

17. The system of claim 16, wherein the graphical image also represents a position of the distal tip of the elongate percutaneously introducible device.

18. The system of claim 17, wherein the percutaneously deliverable vascular device is a filter, stent, stent valve, occluder, embolization device, or anastomosis device.

19. The system of claim 1, wherein the elongate percutaneously introducible device includes one or more visible markers on a proximal end of the device, and wherein said computer processor and display device are configured to correlate a position of the intravascular ultrasound probe on the reference scale with the one or more visible markers.

\* \* \* \* \*